US 6,689,356 B1

(12) United States Patent
Zlotkin et al.

(10) Patent No.: US 6,689,356 B1
(45) Date of Patent: Feb. 10, 2004

(54) RECOMBINANT BACULOVIRUSES PRODUCING INSECT TOXINS

(75) Inventors: Eliahu Zlotkin, Mevasert Zion (IL); Susumu Maeda, Davis, CA (US); Billy Fred McCutchen, Wilimington, DE (US); Bruce D. Hammock, Davis, CA (US); Elizabeth Fowler, Durham, NC (US); Rama M. Belagaje, Indianapolis, IN (US)

(73) Assignees: The Regents of the Unviersity of California, Oakland, CA (US); BASF Aktiengesellschaft, Ludwigshafen (DE)

( * ) Notice: Subject to any disclaimer, the term of this patent is extended or adjusted under 35 U.S.C. 154(b) by 102 days.

(21) Appl. No.: 08/472,053

(22) Filed: Jun. 6, 1995

Related U.S. Application Data

(63) Continuation-in-part of application No. 08/229,417, filed on Apr. 15, 1994, now abandoned, which is a continuation-in-part of application No. 07/629,603, filed on Dec. 19, 1990, now abandoned, which is a continuation-in-part of application No. 07/286,087, filed on Dec. 19, 1988, now abandoned.

(51) Int. Cl.[7] ............ A61K 48/00; C12N 15/866; C12N 15/63

(52) U.S. Cl. .......... 424/93.2; 424/93.1; 424/93.6; 435/5; 435/6; 435/69.1; 435/320.1; 435/455; 435/456; 435/325; 435/348; 435/91.1; 435/91.4; 435/91.41

(58) Field of Search ............ 435/69.1, 172.1, 435/172.3, 320.1, 235.1, 5, 6, 455, 456, 325, 348, 91.1, 91.4, 91.41; 424/93.1, 93.2, 93.6

(56) References Cited

U.S. PATENT DOCUMENTS

| | | | |
|---|---|---|---|
| 4,668,511 A | 5/1987 | Aspirot et al. | 424/93.6 |
| 4,745,051 A | 5/1988 | Smith et al. | 435/69.51 |
| 4,762,547 A | 8/1988 | Iwasaki et al. | 504/330 |
| 4,870,023 A | 9/1989 | Fraser et al. | 435/235.1 |
| 4,888,340 A | 12/1989 | Neh et al. | 514/403 |
| 4,929,718 A | 5/1990 | Possani et al. | 530/326 |
| 5,071,748 A | * 12/1991 | Miller | 435/69.1 |
| 5,098,706 A | 3/1992 | Hammock et al. | 424/93.2 |
| 5,162,308 A | 11/1992 | Brown et al. | 514/63 |
| 5,177,308 A | 1/1993 | Barton et al. | 800/205 |
| 5,180,581 A | 1/1993 | Miller et al. | 424/93.2 |
| 5,238,724 A | 8/1993 | Bjostad, III et al. | 424/84 |
| 5,266,314 A | 11/1993 | Maeda | 424/93.2 |
| 5,266,317 A | * 11/1993 | Tomalski et al. | 424/93.2 |

FOREIGN PATENT DOCUMENTS

| | | |
|---|---|---|
| EP | 0222412 B | 11/1986 |
| EP | 0225777 A | 12/1986 |
| GB | 2074868 A | 3/1981 |

OTHER PUBLICATIONS

Moffat, Anne Simon, "New Chemicals Seek to Outwit Insect Pests," *Science*, 261, pp. 550–551 (1993).
Zlotkin, "Toxins Derived from Arthropod Venoms Specifically Affecting Insects," Chapter 15 in *Comprehensive Insect Physiology, Biochemistry & Pharmacology*, vol. 10, pp. 499–541 (1985).
Piek et al., "The Pharmacology of Microbracon Venom," *Comp. Biochem. Physiol.*, vol. 72C, pp. 303–309 (1982).
Maeda, "Increased Insecticidal Effect by a Recombinant Baculovirus Carrying a Synthetic Diuretic Hormone Gen," *Biochemical and Biophysical Research Communications*, 165:3, pp. 1177–1183 (1989).
Miller et al., "Bacterial Viral, and Fungal Insecticides," *Science*, 219, pp. 715–721, (Feb. 11, 1983).
Carbonell et al., "Synthesis of a Gene Coding for an Insect–Specific Scorpion Neurotoxin and Attempts to Express it Using Baculovirus Vectors," *Gene*, 73, pp. 409–418 (1988).
Dee et al., "Expression and Secretion of a Functional Scorpion Insecticidal Toxin in Cultured Mouse Cells," *Bio/Technology*, 8, pp. 339–342, (Apr. 1990).
Gordon et al., "The Binding of the Insect Selective Neurotoxin (AaIT) from Scorpion Venom to Locust Synaptosomal Membranes," *Biochimica et Biophysica Acta*, 778, pp. 349–358 (1984).
Sakurai et al., "Complete Nucleotide Sequence of Gene for Sex–Specific Storage Protein of *Bombyx mori*," *Nucleic Acids Research*, 16:15, pp. 7717–7718 (1988).
Adachi et al., "cDNA Structure and Expression of Bombyxin, an Insulin–like Brain Secretory Peptide of the Silkmoth *Bombyx mori*," *The Journal of Biological Chemistry*, 264:13, pp. 7681–7685, (May 5, 1989).
Merryweather et al., "Construction of Genetically Engineered Baculovirus Insecticides Containing the *Bacillus thuringiensis* subsp. *kurstaki* HD–73 Delta Endotoxin," *Journal of General Virology*, 71, pp. 1535–1544 (1990).
Martens et al., "Insecticidal Activity of a Bacterial Crystal Protein Expressed by a Recombinant Baculovirus in Insect Cells," *Applied and Environmental Microbiology*, 56:9, pp. 2764–2770, (Sep. 1990).

(List continued on next page.)

*Primary Examiner*—David Guzo
(74) *Attorney, Agent, or Firm*—Ginger R. Dreger; Heller Ehrman White & McAuliffe, LLP

(57) ABSTRACT

A recombinant baculovirus is provided with a genetic coding sequence for the production of a foreign protein that is toxic to insects. Preferred are nuclear polyhedrosis viruses, with preferred embodiments having been constructed and expressed in insect cells: BmNPV.AaIT and AcNPV.AaIT. Both embodiments function in insect cells infected therewith so as to have the toxin AaIT (originating from the venom of the scorpion *A. australis*) secreted. A clone designated (pCIB4223), which contains the *Bombyx mori* signal sequence fused to the AaIT sequence, has been deposited with the American type culture collection and designated "ATCC 40906."

17 Claims, 21 Drawing Sheets

OTHER PUBLICATIONS

Tomalski and Miller, "Insect Paralysis by Baculovirus–Mediated Expression of a Mite Neurotoxin Gene," *Nature*, 352, pp. 82–85, (Jul. 4, 1991).

McCutchen et al., "Development of a Recombinant Baculovirus Expressing an Insect–Selective Neurotoxin: Potential for Pest Control," *Bio/Technology*, 9, pp. 848–852, (Sep. 1991).

Maeda et al., "Insecticidal Effects of an Insect–Specific Neurotoxin Expressed by a Recombinant Baculovirus," *Virology*, 184, pp. 777–780, (1991).

Stewart et al., "Construction of an Improved Baculovirus Insecticide Containing an Insect–Specific Toxin Gene," *Nature*, 352, pp. 85–88, (Jul. 4, 1991).

Hammock et al., "The Role of Juvenile Hormone Metabolism in the Metamorphosis of Selected Lepidoptera," *Chemical Abstracts*, 102 (1985), entry 76006b.

Abdel–Aal and Hammock, "3–Octylthio–1,1,1–trifluoro–2–propanone, A High Affinity and Slow Binding Inhibitor of Juvenile Hormone Esterase from *Trichoplusia ni* (Hüber)," *Insect Biochem.*, 15:1 (1985), pp. 111–122.

Abdel–Aal and Hammock, "Transition State Analogs as Ligands for Affinity Purification of Juvenile Hormone Esterase," *Science*, 233 (Sep. 1986), pp. 1073–1076.

Bachmair and Varshavsky, "The Degradation Signal in a Short–Lived Protein," *Cell*, 56 (Mar. 1989), pp. 1019–1032.

Cheung and Hammock, "Micro–Lipid–Droplet Encapsulation of *Bacillus thuringiensis* subsp. *israelensis* δ–Endotoxin for Control of Mosquito Larvae," *Appl. & Environ. Microbiol..*, 50:4 (Oct. 1985), pp. 984–988.

Chiang and Dice, "Peptide Sequences that Target Proteins for Enhanced Degradation During Serum Withdrawal," *J. of Biol. Chem.*, 263:14 (May 1988), pp. 6797–6805.

Hammock and Sparks, "A Rapid Assay for Insect Juvenile Hormone Esterase Activity," *Analytical Biochemistry*, 82 (1977), pp. 573–579.

Hammock et al., "Expression and Effects of the Juvenile Hormone Esterase in a Baculovirus Vector," *Nature*, 344:6265 (Mar. 1990), pp. 458–461.

Hammock and Rose, "Analysis of Juvenile Hormone Esterase Activity," Chpt. 32, pp. 487–495 in Law et al. (Eds.), *Methods in Enzymology*, vol. III: *Steroids and Isoprenoids* (Part B), Academic Press (1985).

Hammock et al., "Trifluoromethylketones as Possible Transition State Analog Inhibitors of Juvenile Hormone Esterase," *Pesticide Biochem. & Physiology*, 17 (1982), pp. 76–88.

Hammock et al., "Selective Inhibition of JH Esterases from Cockroach Hemolymph," *Pesticide Biochem. & Physiology*, 7 (1977), pp. 517–530.

Hammock et al., "Strategies for the Discovery of Insect Control Agents: . . ." Chpt. 12 in Steffens et al. (Eds), *Biomechanism Regulating Growth & Development*, USDA Beltsville Symp. vol. 12, Kluwer Academic Press (1988).

Hanzlik et al., "Isolation and Sequencing of cDNA Clones Coding for Juvenile Hormone Esterase from *Heliothis virescens*," *J. of Biol. Chem.*, 264:21 (Jul. 1989), pp. 12419–12425.

Hanzlik and Hammock, "Characterization of Affinity–purified Juvenile Hormone Esterase from *Trichoplusia ni,*" *J. Biol. Chem.*, 1987:23 (Oct. 1987), pp. 12584–13591.

Huynh et al., "Constructing and Screening cDNA Libraries in λgt10 and λgt11," Chpt. 2, IRL Press (Oxford), (1985), pp. 49–78.

Ichinose et al., Pharmacokinetic Studies of the Recombinant Juvenile Hormone Esterase in *Manduca sexta*, *Pesticide Biochem. & Physiology*, 42 (1992), pp. 13–23.

Ichinose et al., "Uptake of Juvenile Hormone Esterase by Pericardial Cells of *Manduca sexta*," submitted to *Insect Biochem. Molec. Biol.* (1992).

Philpott and Hammock, "Juvenile Hormone Esterase is a Biochemical Anti–Juvenile Hormone Agent," *Insect Biochem.*, 20:5 (1990), pp. 451–459.

Rogers et al., "Amino Acid Sequences Common to Rapidly Degraded Proteins: The PEST Hypothesis," *Science*, 234 (Oct. 1986), pp. 364–368.

Sparks and Hammock, "Induction and Regulation of Juvenile Hormone Esterase During the Last Larval Instar of the Cabbage Looper, *Trichoplusia ni,*" *J. Insect. Physiolo.*, 25 (1979), pp. 551–560.

Sparks and Hammock, "Comparative Inhibition of the Juvenile Hormone Esterases from *Trichoplusia ni, Tenebrio molitor*, and *Musca domestica,*" *Pesticide Biochem. & Physiology*, 14 (1980), pp. 290–302.

Wozniak and Jones, "Immunochemical Characterization of Juvenile Hormone Esterase from Different Species of Lepidoptera," *Biochem. & Biophys. Res. Commun.*, 144:3 (May 1987), pp. 1281–1286.

Wroblewski et al., "Regulation of Juvenile Hormone Esterase Gene Expression in the Tobacco Budworm (*Heliothis virescens*)," *Archives of Biochem. & Biophys.*, 278:2 (May 1990), pp. 461–466.

Eldridge et al., "Insecticidal Properties of Genetically Engineered Baculoviruses Expressing and Insect Juvenile Hormone Esterase Gene," *Appl. & Environ. Microbio.*, 58:5 (May 1992), pp. 1583–1591.

Hayakawa, "Structure of a Growth–Blocking Peptide Present in Parasitized Insect Hemolymph," *J. of Biol. Chem.*, 266:13 (May 5, 1991), pp. 7982–7984.

Hayakawa, "A Putative New Juvenile Peptide Hormone in Lepidopteran Insect," *Biochemical and Biophysical Research Communications*, 185:3 (Jun. 30, 1993), pp. 1141–1147.

Smith et al., "Production of Human Beta Interferon in Insect Cells Infected with a Baculovirus Expression Vector," *Mol. Cell Biol.*, 3 (1983), pp. 2156–2165.

Betana et al., "Potential of Baculo Viruses Expressing a Scorpion Toxin and an Esterase in Agriculture . . . ," *Abstr. Pap. Am. Chem. Soc.*, (206 Meet., Pt. 1, (AGR0122), 1993 (Abstract only).

Hayakawa, "Juvenile Hormone Esterase Activity Repressive Factor in the Plasma of Parasitized Insect Larvae," *J. Biol. Chem.*, 265:19 (1990), pp. 10812–10816.

Hayakawa, "Juvenile Hormone Esterase Activity Repressive Peptide in the Parasitized Insect Larvae," *Zool. Sci.* (Toyko), 7:6 (1990), p. 1061 (Abstract only).

Ward et al., "Analysis of the Catalytic Mechanism of Juvenile Hormone Esterase by Site–Directed Mutagenesis," *Int. J. Biochem.* (England), 24:12 (Dec. 1993), pp. 1933–1941 (Abstract only).

Hammock et al., "Development of Recombinant Viral Insecticides by Expression of an Insect–Speicfic Toxin . . . ," *Arch. Insect Biochem. Physiol.* (US), 22:3–4 (1993), pp. 315–44 (Abstract only).

Possee et al., "Expression of the Proteins with Insecticidal Activities Using Baculo Virus Vectors . . . ," *Ann. N.Y. Acad. Sci.*, 646 (1991), pp. 234–239 (Abstract only).

Hammock et al., "Improving the Efficacy of Baculo Virus Insecticides by Expressing with Insect Selective Proteins," *Abstr. Pap. Am. Chem. Soc.* (202 Meet., Pt. 1, AGR09) (1991) (Abstracat only).

Bonning et al., "Further Development of a Recombinant Baculovirus Insecticide Expressing the Enzyme JHE from Heliothis–Virescens," *Biochem. Mol. Biol.*, 22:5 (1992) pp. 453–458 (Abstract only).

McCutchen et al., "Development of Surrogate Substrates for Juvenile Hormone Esterase," *Archives of Biochemistry and Biophysics*, 307:2 (Dec. 1993), pp. 231–241.

Abdel–Aal and Hammock, "Apparent Multiple Catalytic Sites Involved in the Ester Hydrolysis of Juvenile Hormones by the Hemolymph and . . . ," *Arch. Biochem. Biophys.*, 243:1 (1985), pp. 206–219.

Touhara et al., "Ligand Binding by a Recombinant Insect Juvenile Hormone Binding Protein," *Biochem.*, 32:8 (1993), pp. 2068–2075.

McCutchen et al., "Recombinant Baculovirus Expressing an Insect–selective Neurotoxin: . . . ," in *Natural & Engineered Pest Management Agents* (Hedin et al., eds), ACS Sympo. Series #551, Am. Chem. Soc., (1994) pp. 348–367.

Heinz et al., "Direct Effects of Recombinant Nuclear Polyhedrosis Viruses on Selected Non–Target Organisms," *J. Econ. Entomol.*, 88:2, (1995), pp. 259–264.

Hammock, "Recombinant Baculoviruses as Biological Insecticides," in *Pest Management: Bioloically Based Technologies* (Lumsden and Vaughn, eds.), ACS Symp. Series, Am. Chem. Soc., (1993), pp. 313–325.

Bonning and hammock, "Lethal Ratios: An Optimized Strategy for Presentation of Bioassay Data Generated from Genetically Engineered Baculoviruses," *J. Invert. Pathol.*, 62 (1993), pp. 196–197.

Maeda et a l., "Recombinant Baculoviruses Expressing Foreign Genes for . . . ," in *Pest Control with Enhanced Environmental Safety*, (Duke et al., eds.), ACS Sympos. Series #524, Am. Chem. Soc. (1993), pp. 281–297.

Bonning and Hammock, "Development and Potential of Genetically Engineered Viral Insecticides," *Biotechnol. Genetic Engeinnering Rev.*, 10 (1992), pp. 455–489.

Hammock et al., "Cloning, Expression and Biolgoical Activity of the JHE from *Heliothis virescens*," in *Molecular Insect Science* (Hagedorn et al., eds.), Plenum Press (1990), pp. 49–56.

Bonning et al., "Superior Expression of JHE and β–Galactosidase from the Basic Protein Promoter of *Autographa californica* Nuclear Polyhedrosis Virus Compared to the . . . ," *J. Gen. Virol.*, 75 (1994), pp. 1551–1556.

Harshman et al., "Cloning, Characterization and Genetics of the JHE Gene from *Heliothis virescens*," *Insect. Biochem. Molec. Biol.*, 24:7 (1994), pp. 671–676.

Ichinose et al., "Pharmacokinetics and Tissue Uptake of the Recombinant JHE in Insects" in *Pesticides/Environment*: . . . , (Mitsui et al., eds.), Proc. of 1st Int'l. Symp. on Pest. Sci., Pesticide Sci. Soc. of JP (1993).

Bonning et al., "Insect Control by Use of Recombinant Baculoviruses Expressing JHE," in *Natural and Engineered Pest Management Agents* (Hedin et al., eds.), ACS Symp. Ser. #551, Am. Chem. Soc. (1994), pp. 368–383.

Roelvink et al., "Dissimilar Expression of *Autographa californica* Multiple Nucleocapsid Nuclear Polyhedrosis Virus Polyhedrin and p10 Gene," *J. Gen. Virol.*, 73 (1992), pp. 1481–1489.

Booth et al., Localization of JHE During Development in Normal and in Recombinant Baculovirus–Infected Larvae of the Moth *Trichoplusia ni, Tissue & Cell*, 24:2 (1992), pp. 267–282.

Harshman et al., "Effects of Recombinant Juvenile Hormone Esterase on *Aedes aegypti*," *Proc. Calif. Mosq. Vector Control Assoc.*, (1991), pp. 77–80.

Hammock, "Regulation of Juvenile Hormone Titer: Degradation," in *Comprehensive Insect Physiology, Biochemistry, and Pharmacology* (Kerkut and Gilbert, eds.) Pergamon Press (1985), pp. 431–472.

Jones and Hammock, "Prepupal Regulation of Juvenile Hormone Esterase through Direct Induction by Juvenile Hormone," *J. Insect Physiol.*, 29:6, (1983), pp. 471–475.

Sparks and Hammock, "A Comparision of the Induced and Naturally Occurring Juvenile Hormone Esterases from Last Instar Larvae of *Trichoplusia ni,*" *Insect Biochem.*, 9, (1979), pp. 411–421.

Spark et al., Effects of the Anti Hormone–Hormone Mimic ETB on the Inductio nof Insect Juvenile Hormone Esterase in *Trichoplusia ni, Life Sci.*, 25 (1979), pp. 445–450.

Zlotkin et al., "The Effect of Scorpion Venom on Blowfly Larvae—A New Method for the Evaluation of Scorpion Venoms Potency," *Toxicon*, 9 (1971), pp. 1–8.

Zlotkin et al., "An Excitatory and a Depressant Insect Toxin from Scorpion Venom both Affect Sodium Conductance and Possess a Common Binding Site," *Arch. Biochem. & Biophys.*, 240:2 (Aug. 1985), pp. 877–887.

Adachi et al., "cDNA Structure and Expressio nof Bombyxin, an Insulin–like Brain Secretory Peptide of the Silkworm *Bombyx mori,*" *J Biol. Chem.*, 264:13 (1984), pp. 349–358.

Carbonell et al., "Baculovirus Interaction with Nontarget Organisms: a Virus–Borne Reporter Gene is Not Expressed in Two Mammalian Cell Lines," *Appl. Environ. Microbiol*, 53:7 (Jul. 1987), pp. 1412–1417.

Cameron et al., "Insect Cell Culture Technology in Baculovirus Expression Systems," *Trends in Biotechnology*, vol. 7 (1989), pp. 66–70.

* cited by examiner

Scorpion Toxin Sequences

| SEQ. ID. NO. | | Sequence |
|---|---|---|
| | Buthoid Scorpion Toxins | |
| 2 | LqhIT2 | [DGYIKRRDGC KVACLIGNEG CDKECKAYGG SYGYCWTWGL ACWCEGLPDD KTWKSETNTC G] |
| 3 | LqqIT2 | [DGYIRKRDGC KLSCLFGNEG CNKECKSYGG SYGYCWTWGL ACWCEGLPDE KTWKSETNTC G] |
| 4 | BjIT2 | [DGYIRKKDGC KVSCIIGNEG CRKECVAHGG SFGYCWTWGL ACWCENLPDA VTWKSSTNTC G] |
| 5 | LqhP35 | [VRDAYIAKNY NCVYECFRDA YCNELCTKNG ASSGYCQWAG KYGNACWCYA LPDNVPIRVP GKCR] |
| | Chaotid Scorpion Toxins | |
| 6 | SmpIT2 | [ALPLSGEYEP CVRPRKCKPG LVCNKQQICV DPK] |
| 7 | SmpCT2 | [VSCTGSRDCY APCKRQTGCT SAKCINKSCK CYGC] |
| 8 | SmpCT3 | [VSCTGSKDCY APCRKQTGCP NAKCINKSCK CYGC] |
| 9 | SmpMT | [VSCTGSKECY APCKKQTGCP NAKCMNRKCK CYGC] |

FIG. 8

Synthesis of Gene for AaIT

SEQ. ID NO. 10
Coding Strand

```
5'   1 [GATCCAAATA ATGAAAAAAA ACGGCTACGC TGTTGACTCT TCTGGCAAAG
                   1                        2
    51 CTCCGGAATG CCTGCTGTCT AACTACTGCA ACAACCAGTG CACTAAAGTT
              3                    4                  5
   101 CATTACGCTG ACAAAGGCTA CTGCTGCCTG CTGTCTTGCT ACTGCTTCGG
                          6                    7
   151 CCTGAACGAC GACAAAAAAG TTCTGGAAAT CTCTGACACT CGTAAATCTT
          8                        9                  10
   201 ACTGCGACAC TACTATCAAC TAATAG]   3'
                        11
```

SEQ. ID NO. 11
Complementary Strand

```
5'   1 [GATCCTATTAGTTG ATAGTAGTGT CGCAGTAAGA TTTACGAGTG TCAGAGATT
                        22                  21                 20
    55 CCAGAACTTT TTTGTCGTCG TTCAGGCCGA AGCAGTAGCA AGACAGCAGG
                         19                       18
   105 CAGCAGTAGC CTTTGTCAGC GTAATGAACT TTAGTGCACT GGTTGTTGCA
                17                   16                    15
   155 GTAGTTAGAC AGCAGGCATT CCGGAGCTTT GCCAGAAGAG TCAACAGCGT
                          14                       13
   201 AGCCGTTTTT TTTCATTATT TG]   3'
                 12
```

FIG. 9A

| SEQ. ID NO.'s | |
|---|---|
| Fragments Synthesized | |
| 12 | [GATCCAAATAATGAAAAAAACGG] |
| 13 | [CTACGCTGTTGACTCTTCTG] |
| 14 | [GCAAAGCTCCGGAATGCCTG] |
| 15 | [CTGTCTAACTACTGCAACAA] |
| 16 | [CCAGTGCACTAAAGTTCATT] |
| 17 | [ACGCTGACAAGGCTACTGC] |
| 18 | [TGCCTGCTGTCTTGCTACTG] |
| 19 | [CTTCGGCCTGAACGACGACA] |
| 20 | [AAAAGTTCTGGAAATCTCT] |
| 21 | [GACACTCGTAAATCTTACTG] |
| 22 | [CGACACTACTATCAACTAATAG] |
| 23 | [CGTAGCCGTTTTTTTTCATTATTTG] |
| 24 | [TTTGCCAGAAGAGTCAACAG] |
| 25 | [GACAGCAGGCATTCCGGAGC] |
| 26 | [ACTGGTTGTTGCAGTAGTTA] |
| 27 | [AGCGTAATGAACTTTAGTGC] |
| 28 | [AGGCAGCAGTAGCCTTTGTC] |
| 29 | [CGAAGCAGTAGCAAGACAGC] |
| 30 | [TTTTTTGTCGTCGTTCAGGC] |
| 31 | [GTGTCAGAGATTTCCAGAAC] |
| 32 | [TGTCGCAGTAAGATTTACGA] |
| 33 | [GATCCTATTAGTTGATAGTAG] |

FIG. 9B

SEQ. ID NO. 34
Final Gene

```
          10              20              30              40              50              60
 1  [GATCCAAATAATGAAAAAAACGGCTACGCTGTTGACTCTTCTGGCAAAGCTCCGGAATG]
     ----+----+----+----+----+----+----+----+----+----+----+----+
     GTTTATTACTTTTTTTGCCGATGCGACAACTGAGAAGACCGTTCGAGGCCTTAC
         M  K  K  N  G  Y  A  V  D  S  S  G  K  A  P  E  C 70              80              90             100             110             120
61  [CCTGCTGTCTAACTACTGCAACAACCAGTGCACTAAAGTTCATTACGCTGACAAAGGCTA]
     ----+----+----+----+----+----+----+----+----+----+----+----+
     GGACGACAGATTGATGACGTTGTTGGTCACGTGATTTCAAGTAATGCGACTGTTTCCGAT
      L  L  S  N  Y  C  N  N  Q  C  T  K  V  H  Y  A  D  K  G  Y 130             140             150             160             170             180
121 [CTGCTGCCTGCTGTCTTGCTACTGCTTCGGCCTGAACGACGACAAAAAGTTCTGGAAAT]
     ----+----+----+----+----+----+----+----+----+----+----+----+
     GACGACGGACGACAGAAACGATGACGAAGCCGGACTTGCTGCTGTTTTTTCAAGACCTTTA
      C  C  L  L  S  C  Y  C  F  G  L  N  D  D  K  K  K  V  L  E  I 190             200             210             220             230
181 [CTCTGACACTCGTAAATCTTACTGCGACACTACTATCAACTAATAG]
     ----+----+----+----+----+----+----+----+----+
     GAGACTGTGAGCATTTAGAATGACGCTGTGATGATAGTTGATTATCCCTAG
      S  D  T  R  K  S  Y  C  D  T  T  I  N  *  *
```

FIG. 9C

SEQ. ID NO. 43

Gene Encoding LqhIT2 Insect Toxin

```
         10             20             30             40             50             60
 1  [GATCCATGGACGGCTACATCAAGCGCCGCGACGGGCTGCAAGGTGGCTGCCTGATCGGCA]
    ----+----|----+----|----+----|----+----|----+----|----+----|
    GTACCTGCCGATGTAGTTCGCGGCGCTGCCCGACGTTCCACCGACGGACTAGCCGT
     M  D  G  Y  I  K  R  R  D  G  C  K  V  A  C  L  I  G  N 70             80             90            100            110            120
61  [ACGAGGGCTGCGACAAGGAGTGCAAGGCTTACGGCAGCTACGGCTACTGCTGGACCT]
    ----+----|----+----|----+----|----+----|----+----|----+----|
    TGCTCCCGACGCTGTTCCTCACGTTCCGAATGCCGTCGATGCCGATGACGACCTGGA
     E  G  C  D  K  E  C  K  A  Y  G  G  S  Y  G  Y  C  W  Y  W 130            140            150            160            170            180
121 [GGGGCCTGGCTTGCTGGTGTGCGAGGGCCTGCCCGACGACAAGACCTGGAAGAGCGAGACCA]
    ----+----|----+----|----+----|----+----|----+----|----+----|
    CCCCGGACCGAACGACCACACGCTCCCGGACGGGCTGCTGTTCTGGACCTTCTCGCTCTGGT
     G  L  A  C  W  C  E  G  L  P  D  D  K  T  W  K  S  E  T  N 190            200
181 [ACACCTGCGGGCTAATAG] 201
    ----+----|----+---
    TGTGGACGCCCGATTATCCCTAG
     T  C  G  *  *
```

FIG. 10 pCIB 4223
pBK283 + Bombyxin signal + AaIT

FIG. 12

SEQ. ID NO. 39 pCIB 4223

(Bombyxin signal sequence and AaIT peptide)

``` pINIII-ompA-AaIT
Expression Vector for ompA Leader-AaIT Fusion Protein

SEQ. ID NO. 44

PR-1a LEADER/AaIT GENE

```
  1 [GAATTCATTC AAGATACAAC ATTTCTCCTA TAGTCATGAA AAAAAACGGC TACGCTGTTG]
    (EcoRI)    (29 bp PR-1a leader)           M  K  N  G   Y  A  V  D 61 [ACTCTTCTGG CAAAGCTCCG GAATGCCTGC TGTCTAACTA CTGCAACAAC CAGTGCACTA]
     T  L  L  G  K  A  P   E  C  L  L   S  N  Y   C  N  N   Q  C  T 121 [AAGTTCATTA CGCTGACAAA GGCTACTGCT GCCTGCTGTC TTGCTACTGC TTCGGCCTGA]
     K  F  I  T   L  T  K   A  T  A   A  C  C  L   C  Y  C   F  G  L  N 181 [ACGACGACAA AAAAGTTCTG GAAATCTCTG ACACTCGTAA ATCTTACTGC GACACTACTA]
     T  T  T  K   K  V  L   E  I  S  D   T  R  K   S  Y  C   D  T  T  I

241 [TCATCAACTA GTAATCTAGA ATTC] 264
     I  N  *
```

FIG. 15
PANEL A

Double 355 Promoter and tml 3" End Cassette

PANEL B

PANEL C

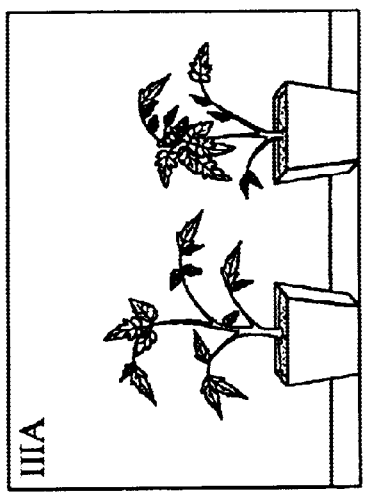
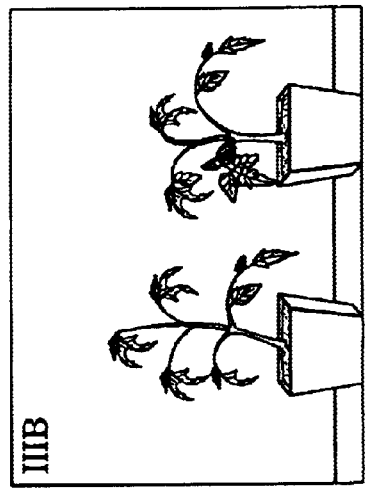
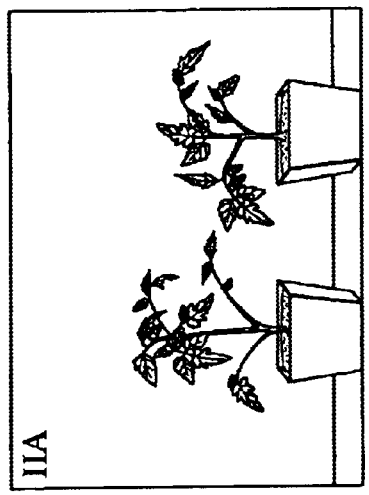
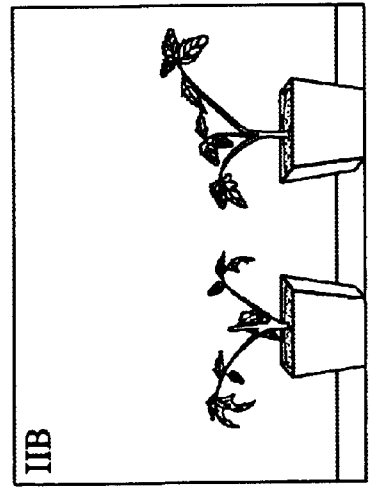
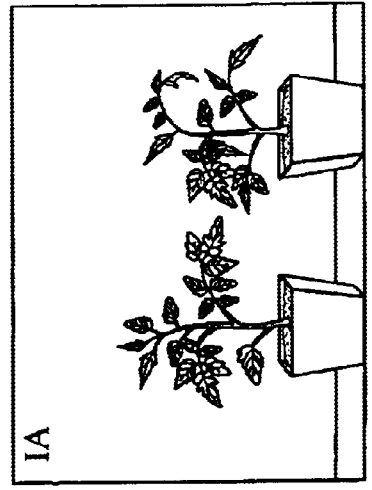
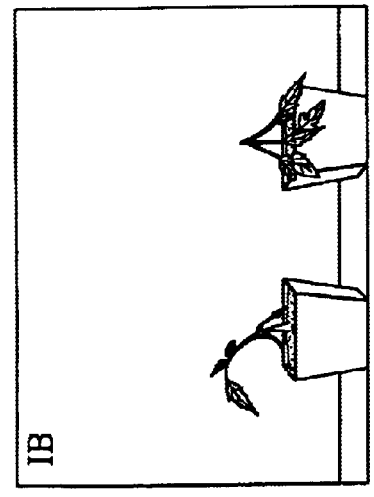
FIG. 17

RECOMBINANT BACULOVIRUSES PRODUCING INSECT TOXINS

This application is a continuation-in-part of application Ser. No. 08/229,417, abandoned filed Apr. 15, 1994, which is a continuation-in-part of application Ser. No. 07/629,603 filed Dec. 19, 1990, abandoned, which is a continuation-in-part of Ser. No. 07/286,087, filed Dec. 19, 1988, abandoned.

This invention was made with Government support under Grant Nos. 91-37302-6168 and NAPIAP R8-27, awarded by the United States Department of Agriculture. The Government has certain rights in this invention.

FIELD OF THE INVENTION

The present invention relates to insecticidal microbes with enhanced insecticidal activity. More particularly, the present invention relates to insecticidal baculoviruses in which a genetic sequence coding for an insect selective toxin has been introduced into the genome of the baculovirus.

BACKGROUND OF THE INVENTION

Venom is defined as a mixture of substances which are produced in specialized glandular tissues in the body of a venomous animal. The venom may be introduced into the body of its prey or opponent, such as by the aid of a stinging-piercing apparatus, in order to paralyze and/or kill it, although other means of delivering venom are known. Scorpions, for example, contain in their venom a number of proteins, or neurotoxins, which are toxic and act on the nervous system. The individual neurotoxins differ in their potency on various species of animals.

The venoms derived from scorpions belonging to the Buthinae subfamily have three main groups of polypeptide neurotoxins which modify axonal sodium conductance. One group of neurotoxins are the α-toxins, which specifically affect mammals through an extreme prolongation of the action potentials due to a slowing or blockage of the sodium channel in activation (Catterall, *Science*, 223:653–661 (1984); Rochat et al., *Advances in Cytopharmacology*, pp. 325–334 (1979)). The second group of neurotoxins are the depressant insect selective toxins which induce a progressively developing flaccid paralysis of insects by the blockage of action potentials substantially due to the suppression of sodium current (Lester et al., *Biochim. Biophys. Acta*, 701:370–381 (1982); Zlotkin et al., *Arch. Biochem. Biophys.*, 240:877–887 (1985)). The third group of neurotoxins are the excitatory insect selective toxins which cause an immediate (knock down) spastic paralysis of insects by the induction of repetitive firing in their motor nerves due to an increase of the sodium peak current and the voltage dependent slowing of its inactivation (Walther et al., *J. Insect Physiol.*, 22:1187–1194; Pelhate et al., *J. Physiol.*, 30:318–319 (1981)).

The scorpion venom derived insect toxins were detected and their isolation was monitored by the typical responses of Sarcophaga blowfly larva which develop an immediate and transient contraction paralysis when injected with the excitatory toxins and progressively developing flaccidity for the depressant toxins (Zlotkin et al., *Toxicon*, 9:1–8 (1971); Lester et al., *Biochim. Biophys. Acta*, 701:370–381 (1982)). In spite of the opposite symptomatology induced by the depressant and excitatory insect toxins, both affect exclusively insect sodium channels and share the same binding site (Zlotkin et al., *Arch. Biochem. Biophys.* 240:877–887 (1985); Gordon et al., *Biochim. Biophys. Acta*, 778:349–358 (1984)).

Insect-selective toxins have also been identified in venoms from snails, spiders, and a number of other arthropods. [See review by Zlotkin, *Comprehensive Insect Physiology, Biochemistry and Pharmacology*, Vol. 10, Chapter 15, pp. 499–541 (1985).] The venoms of braconid wasps are highly toxic to lepidopterous larvae. The venom of the braconid Bracon hebetor causes a flaccid paralysis in lepidopterous larvae by inducing presynaptic interruption of the excitatory glutaminergic transmission at the insect neuromuscular junction (Piek et al., *Comp. Biochem. Physiol.*, 72C:303–309 (1982)). The venoms of solitary wasps are toxic to a large number of insects and spiders from different orders (Rathmeyer, *Z. Vergl. Physiol.*, 45:453–462 (1962)). An example of these venoms is the venom of *Philanthus triangulum* which induces in insects a flaccid paralysis substantially due to presynaptic blockage of neuromuscular transmission; this venom affects both excitatory and inhibitory transmission (May et al., *Insect Physiol.*, 25:285–691 (1979)). The venom of the black widow spider, *Latrodectus mactans*, contains components which are neurotoxic to insects, but not to mammals, and other components with the opposite selectivity (Fritz et al., *Nature*, 238:486–487 (1980); Ornberg et al., *Toxicon*, 14:329–333 (1976)).

Polyhedrosis viruses have been identified as potentially useful to express foreign genes in cells. Smith et al., U.S. Pat. No. 4,745,051, discloses a method for producing a recombinant baculovirus expression vector capable of expression of a selected gene in a host insect cell utilizing baculoviruses from *Autographa californica, Trichoplusia ni, Rachiplusia ou*, and *Galleria mellonella*. Bishop, *Trends in Biotech.*, vol. 3 (1988), relates to genetic engineering of baculoviruses for improved pesticidal activity. At page 3, Bishop discusses the possibility of including foreign genes in a nuclear polyhedrosis virus of the alfalfa looper moth *Autographa californica*. Fraser et al., U.S. Pat. No. 4,870,023, relates to recombinant *Autographa californica* and *Heliothis zea* baculoviruses which encode fusion polyhedrin proteins capable of forming occlusion bodies containing foreign peptides. At column 40, Fraser et al. suggest that genes coding for neurotoxins may be expressed in order to increase the insecticidal activity of baculoviruses.

Maeda et al., European Patent Application, publication number 0 222 412, discloses methods of producing insulin-like growth factor I (IGF-1) using recombinant *Bombyx mori* nuclear polyhedrosis viruses. Maeda, in *Invertebrate Cell System Applications*, Vol. I (J. Mitsuhashi, ed., CRC Press, Boca Raton, Fla., 1990) describes gene transfer vectors of the *Bombyx mori* nuclear polyhedrosis virus, and their use for expression of foreign genes in insect cells. Adachi et al., *J. Biol. Chem.*, 264:7681–7685 (1989), relates to the cDNA structure of the bombyxin protein. Maeda, European Patent Application, publication number 0 225 777, with a corresponding U.S. patent issued Nov. 30, 1993 as U.S. Pat. No. 5,266,314, relates to recombinant viruses containing DNA segments of two different nuclear polyhedrosis viruses from different host insects. The recombinant virus is disclosed by Maeda to be effective in destroying or controlling both species of host insects. Maeda, *Biochem. and Biophys. Research Communications*, 165:1177–1183 (1989) discloses that genetically engineered insect viruses containing a recombinant gene encoding the diuretic hormone of the tobacco hornworm resulted in increased insecticidal activity of the baculovirus.

Miller et al., *Science*, 219:715–721 (1983) contains the suggestion that recombinant DNA technology could be used to enhance the toxicity of a virus, for example by introducing an insect-specific toxin gene into the genome of *Autographa californica* nuclear polyhedrosis virus.

Until the present invention, however, attempts to express genes coding for insect-selective neurotoxins and thereby increase the insecticidal activity of recombinant baculoviruses have been unsuccessful. Carbonell et al., *Gene*, 73:409–418 (1988) attempted to use insect-specific scorpion neurotoxins to improve the effectiveness of baculovirus pesticides. Carbonell et al. cloned the gene encoding insectotoxin-1 of the scorpion *Buthus eupeus* in *E. coli*, and attempted to express the gene in *Autographa californica* nuclear polyhedrosis virus. However, Carbonell et al. reported that biological activity of the toxin was not observed, and no paralytic activity was detected. Carbonell et al., *Applied and Environmental Microbiology*, 53:1412–1417 (1987) further report that insect baculoviruses did not express genes in infected mammalian cell lines. Dee et al., *Bio/Technology*, 8:339–342 (1990) report the expression of insecticidal neurotoxin AaIT under the control of a Moloney murine sarcoma virus promoter in cultured mouse cells. However, Dee et al. report that they were unsuccessful in expressing the neurotoxin in *E. coli*.

Thus, the identification of a suitable foreign gene and an appropriate signal sequence that are effective for insect control is crucial for the construction of a baculovirus insecticide.

SUMMARY OF THE INVENTION

In the present invention, the disadvantages of the prior art in being unsuccessful in expressing scorpion neurotoxins in baculoviruses have largely been overcome.

Accordingly, it is one object of the present invention to provide baculoviruses with enhanced insecticidal activity.

It is another object of the present invention to provide expression systems to produce insect-selective scorpion neurotoxins.

The present invention is directed to insecticidal baculoviruses which possess a genetically enhanced toxicity to insects through the introduction of genes which will induce the production of insect-selective toxins, such as those normally found in scorpions, by the baculovirus. This invention further relates to methods of enhancing the toxicity of the insecticidal baculoviruses comprising incorporating into the genome of the baculovirus a recombinant DNA molecule comprising a genetic sequence coding for a toxin selective for insects.

For example, the toxicity of the *Bombyx mori* nuclear polyhedrosis virus may be enhanced by introducing a recombinant. DNA molecule coding for an insect toxin. The coding genetic sequence may be operably linked to a secretion signal sequence in order to aid the toxicity. The signal sequence may be synthesized based on the sequence of an insect protein, for example, the signal sequence of the *Bombyx mori* protein bombyxin.

BRIEF DESCRIPTION OF THE DRAWINGS AND SEQUENCES

Figure 7:
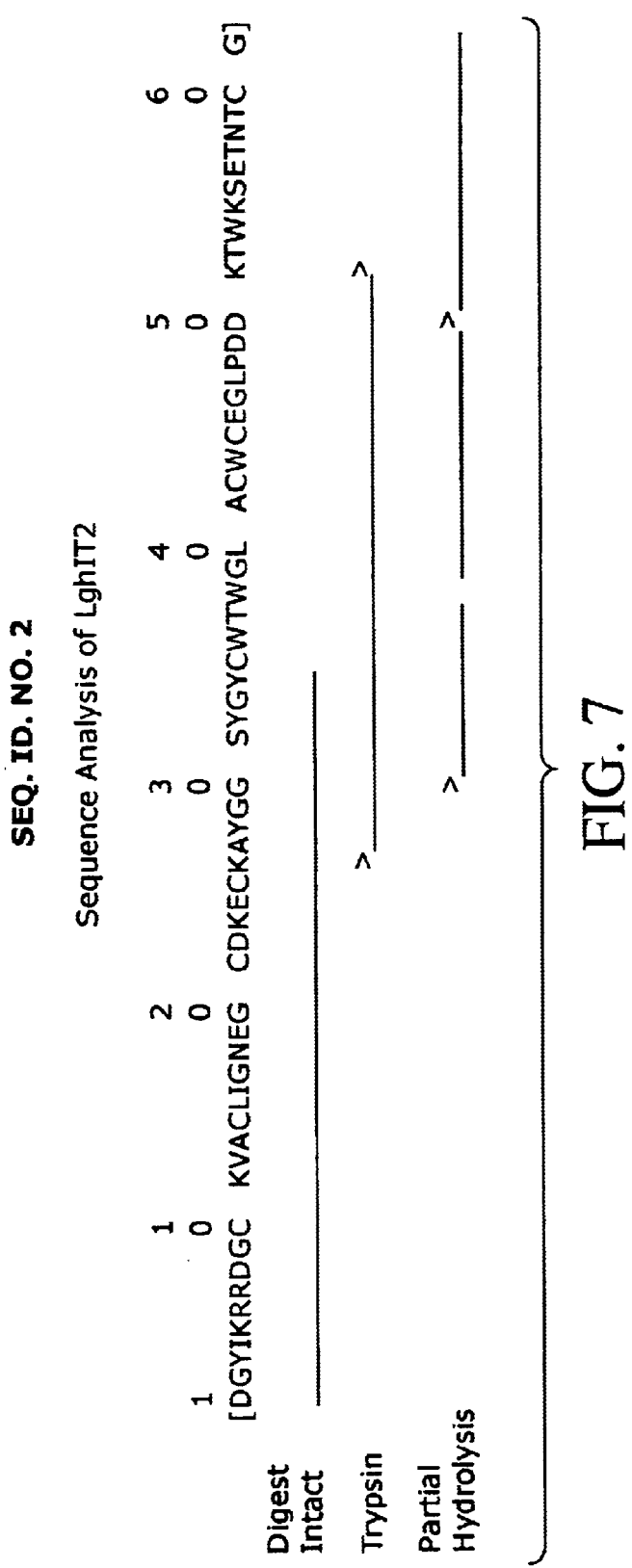

FIG. 7 shows the sequence analysis of LqhIT2 (SEQ ID NO: 2). The solid lines indicate the length of sequence obtained from sequencing particular pieces. Intact denotes the undigested protein; trypsin indicates a peptide isolated from a trypsin digest and partial hydrolysis shows two peptides isolated following dilute acid cleavage.

FIG. 8 shows the amino acid sequences of several scorpion toxins (SEQ ID NOs: 2–9) determined as described in Example 1. LqqIT2 is the representative toxin of Example 1. LqqIT2 is described in Zlotkin et al., *Arch. Biochem. Biophys.*, 240:877–887 (1985). BjIT2 is described by Lester et al., *Biochim. Biophys. Acta*, 701:370–381 (1982). LqhP35 is described in U.S. patent application Ser. No. 07/286,002, filed Dec. 19, 1988 by Zlotkin et al.

The Smp toxins are described in Lazarovici et al., *J. Biol. Chem.*, 257:8397–8404 (1982), Lazarovici, Ph.D. thesis, Hebrew University, Jerusalem (1980), and Lazarovici et al., *Comp. Biochem. Physiol.*, 71C:177–181 (1982).

FIG. 9 Parts A–C shows the synthesis and sequence of the gene for AaIT. SEQ. ID. NO:10 shows the coding strand sequence, while SEQ. ID. NO:11 shows the complementary strand sequence. SEQ. ID. NO:12–33 shows the sequences of the synthesized fragments. SEQ. ID. NOs:34 and 45 shows the sequences of the final gene and the encoded protein, respectively.

FIG. 10 shows the sequences of the gene encoding LqhIT2 insect toxin, which employs the preferred codon frequency for maize (as determined utilizing the Wisconsin GenBank). The resulting gene and encoded protein are designated as SEQ. ID. NO:43 and SEQ. ID. NO:46, respectively.

Figure 11:
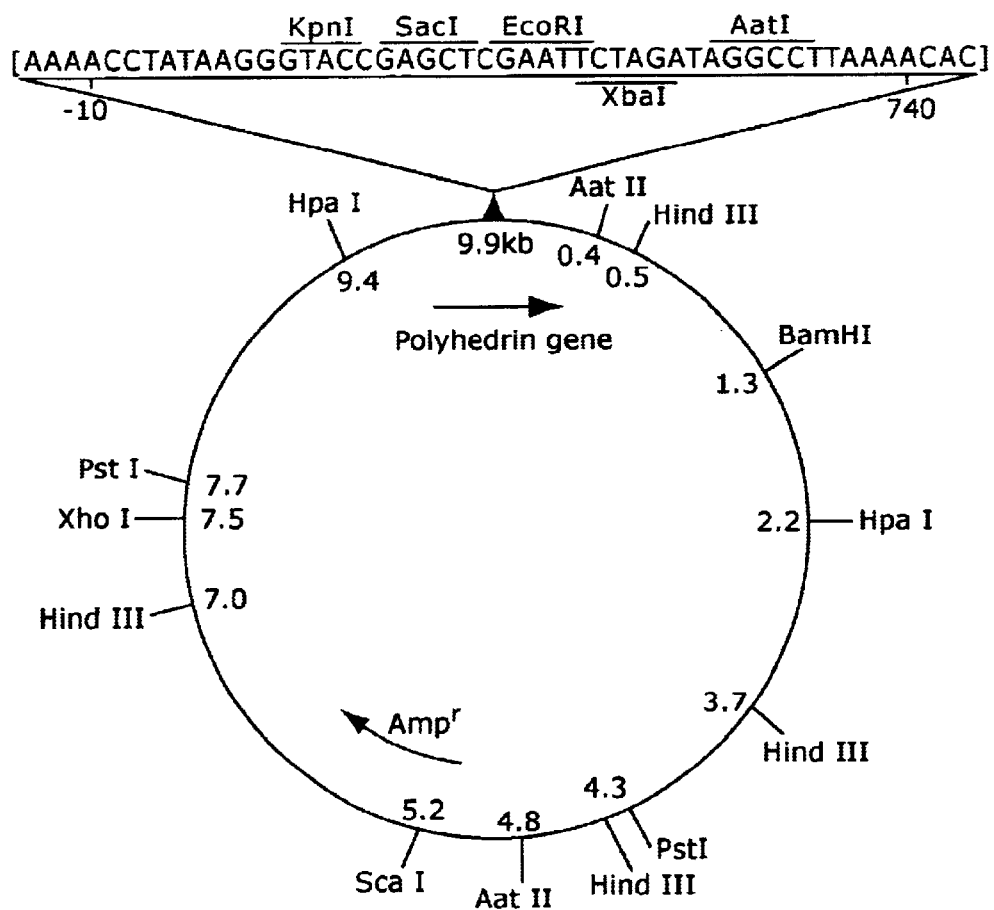

FIG. 11 shows the restriction map of pBK283, the *Bombyx mori* baculovirus transfer vector which includes the DNA insert of SEQ ID NO: 49.

FIG. 12 shows the restriction map of PCIB4223, which is comprised of pBK283, the bombyxin signal sequence and the gene coding for the production of the toxin AaIT.

FIG. 13 shows the DNA sequence (SEQ ID NO: 39) and amino acid sequence (SEQ ID NO: 47) of PCIB4223.

Figure 14:
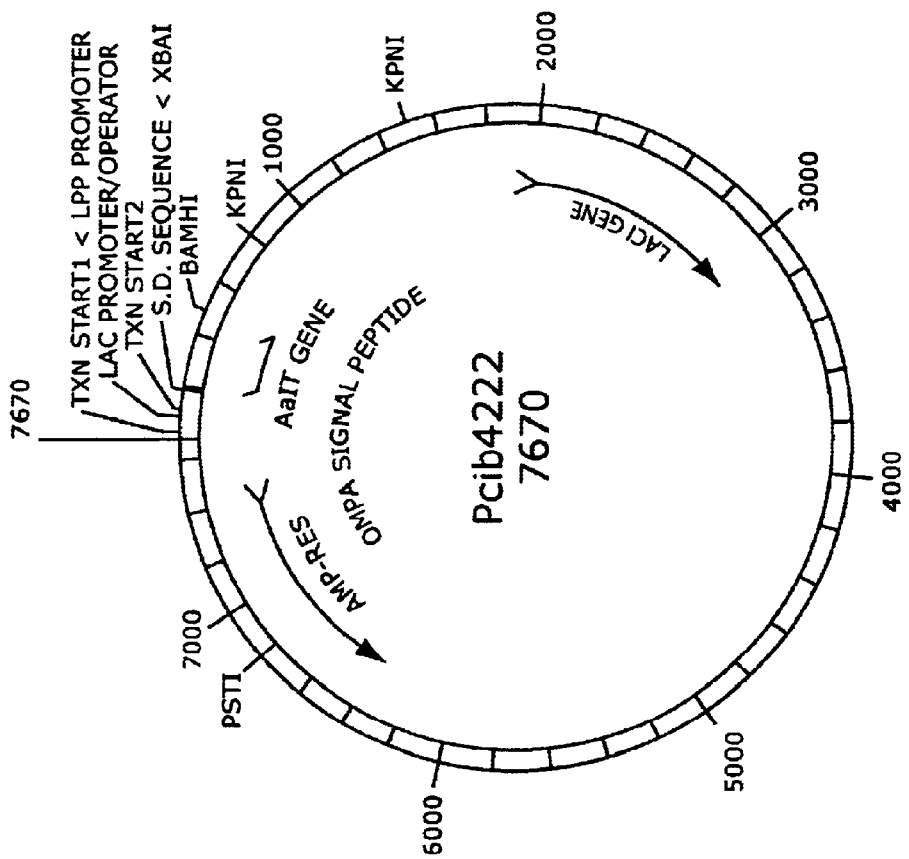

FIG. 14 shows the restriction map of PCIB4222, the expression vector for ompA leader-AaIT fusion protein.

Figure 15:
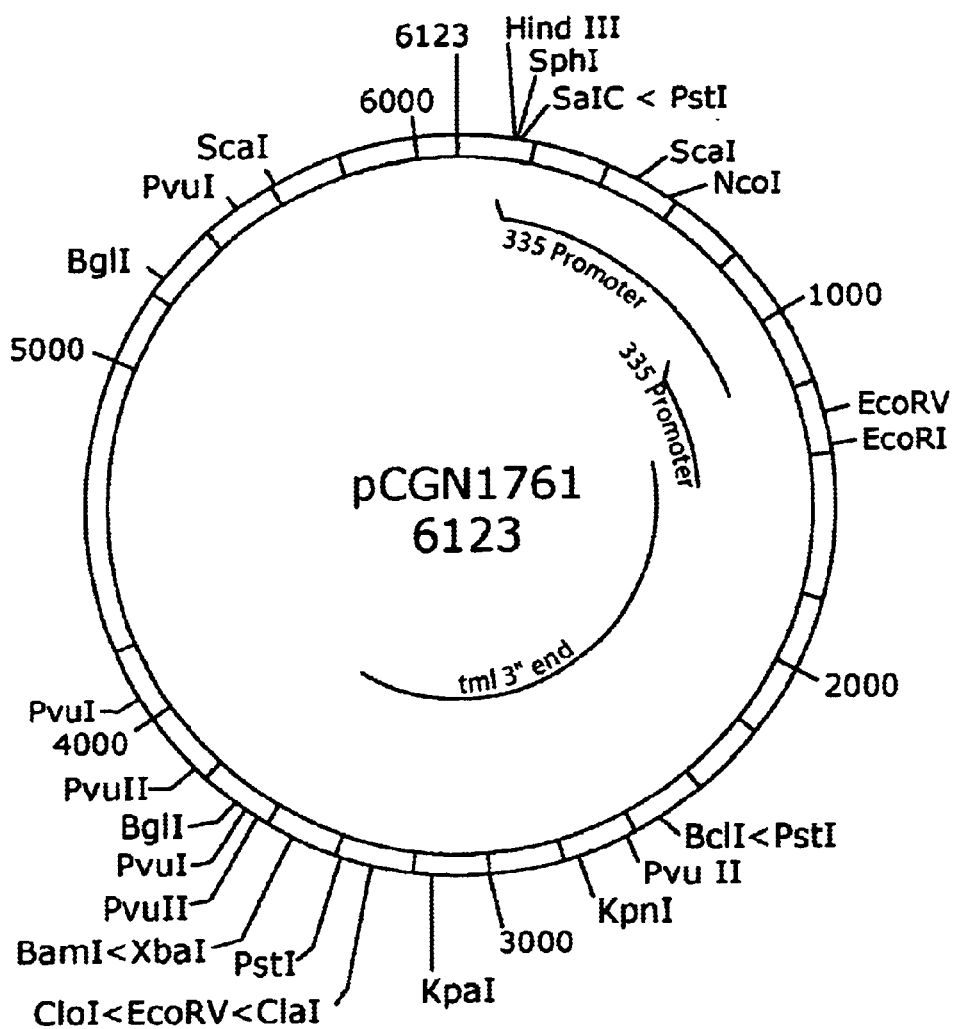
Figure 15:
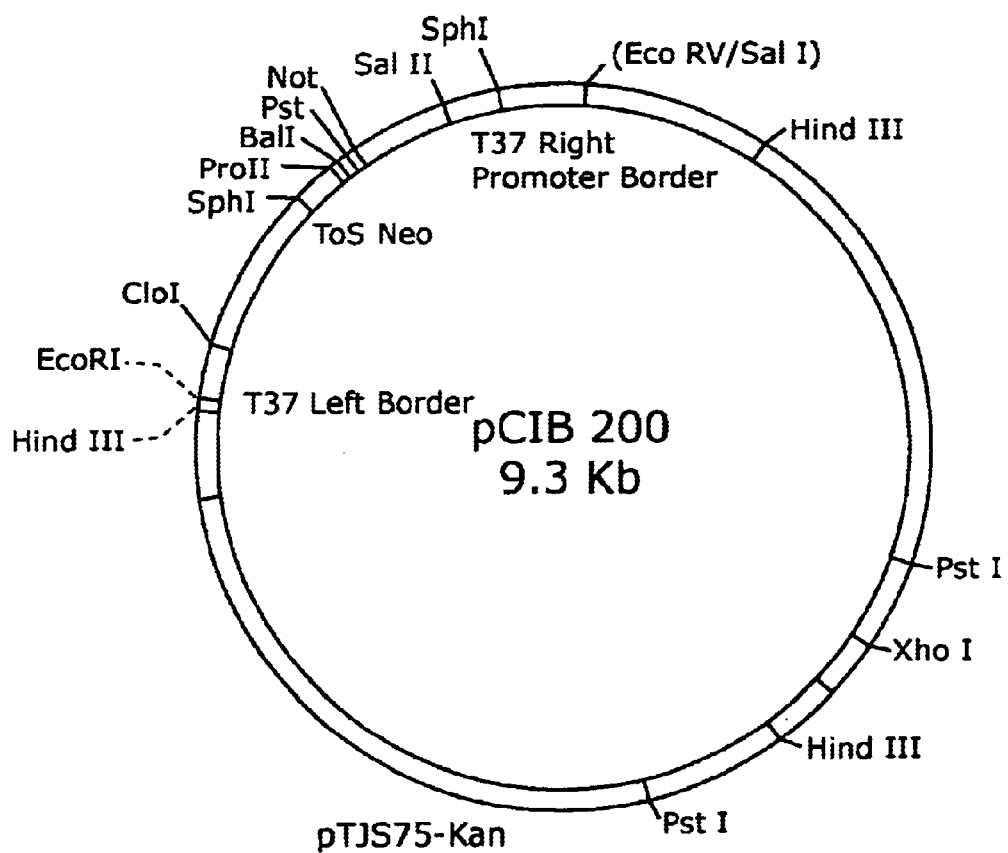

FIG. 15 shows the DNA and amino acid sequence for the PR-1 a leader sequence fused to the AaIT gene (Panel A, SEQ. ID. NOs:44 and 48, respectively); the plasmid map of PCGN1761 (Panel B); and the plasmid map of pCIB200 (Panel C).

Figure 16:
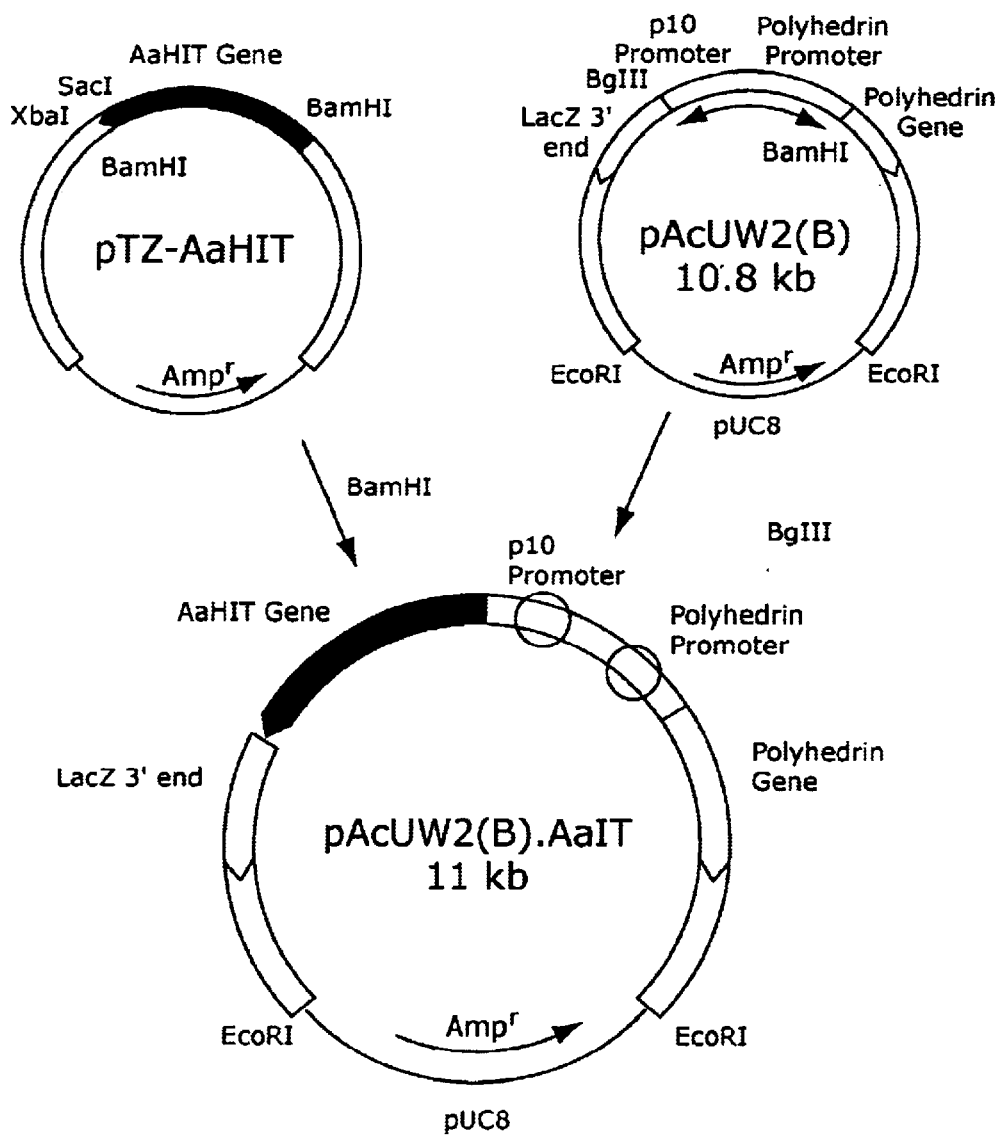

FIG. 16 shows construction of the recombinant transfer vector pAcUW2(B).AaIT.

FIG. 17 illustrates "before and after" larval exposure pictures of tomato plants to illustrate a property of inventive recombinants when used in insect control.

DETAILED DESCRIPTION OF THE PREFERRED EMBODIMENTS

In a preferred embodiment of the present invention, a recombinant baculovirus comprises a genetic coding sequence which encodes for the production of a protein toxic to insects, such as the scorpion insect toxin AaIT, particularly where the baculovirus is a nuclear polyhedrosis virus.

The toxin AaIT from the venom of the scorpion *A. australis* is a single polypeptide chain of 70 amino acids cross-linked by four disulfide bonds. Darbon et al., *Int. J. Peptide Protein Res.*, 20:320 (1982). Although scorpion venom contains various types of toxins, AaIT has toxicity only towards insects and is reported to be non-toxic to isopods and mammals. Zlotkin et al., *Biochimie* (Paris), 53:1073 (1971). Electrophysical and toxin binding studies using insects, crustaceans, and arachnids have demonstrated that AaIT exclusively affects insect nervous systems. Walther et al., *J. Insect Physiol.*, 22:1187 (1976); Tetitelbaum et al., *Insect Biochem.*, 9:343 (1979); Gordon et al., *Biochim. Biophys. Acta*, 778:349 (1984).

Baculoviruses have long been attractive biological agents for insect control, however, one limitation to their use has been the slow speed of killing which allows the pest insects to continue to damage crops. The present invention demonstrates that the incorporation into the virus' genome of a genetic sequence coding for the production of an insect specific scorpion toxin, such as the AaIT toxin, can significantly increase a baculovirus' insecticidal activity in a manner consistent with sodium channel blocking caused by chemical insecticide. The AaIT toxin is also highly insect specific with doses of 1 mg/mouse reported to produce no effects in mice (de Dianous et al. (1987)). This combination of a highly specific insect toxin with a highly selective group of insect viruses presents an aesthetically pleasing approach to crop protection.

The present invention also includes methods of producing insect-selective toxins utilizing expression vector systems. An expression vector is prepared, which expression vector comprises a recombinant DNA molecule which contains a genetic sequence coding for an insect-selective protein neurotoxin. The expression vector is introduced into the genome of an expression system host. Suitable hosts include bacteria such as *E. coli*, and yeast, including the strain *Saccharomyces cerevisiae*. Other suitable expression system hosts include insect cells grown in culture. These insect cells may be infected with a baculovirus. Alternatively, the baculovirus may be used to infect the cells of a living insect, and the insect cells used as the expression system host. The expression system host is then allowed to produce an expression supernatant. The insect-selective toxin may then be isolated from the expression supernatant.

Insect Selective Toxins Derived from Venom.

Recombinant baculoviruses of this invention express a foreign protein in infected insect cells. The expressed foreign protein (which may be a glycoprotein) is an insecticidal toxin, particularly an arthropod or other invertebrate toxin, such as a scorpion toxin, a wasp venom, a snail venom, or a spider venom. A useful scorpion toxin is, for example, that from *Androctonus australis*. A useful snail venom is that from the snail conatoxins (cone shell snail poisons), which the animal delivers by mouth and some individual toxins of which appear to be selective for arthropods including insects. See, for example, Olivera et al., "Diversity of Conus Neuropeptides," *Science*, 249:257–263 (1990).

The amino acid sequence of the excitatory toxin from *Androctonus australis* (AaIT), was determined and the sequence published in Darbon 1982. The AaIT toxin exhibits toxicity to insects, while being non-toxic to isopods and mammals.

Various other scorpion toxins such as of the Buthoid scorpion can also be used according to this invention: LqqIT2 is a depressive insect toxin from *Leiurus quinquestriatus quinquestriatus*. The purification method used to obtain this neurotoxin was published by Zlotkin et al., *Archives of Biochem. Biophys.*, 240:877–887 (1985).

BjIT2 is a depressive insect toxin from *Buthotus judaicus*. The purification has been published in Lester et al., *Biochim. Biophys. Acta*, 701:370–381 (1982). BjIT2 exists in two isoforms which differ in amino acid sequence at position 15. Form 1 has isoleucine in this position while form 2 has valine.

LqhIT2 is a depressive insect toxin from *Leiurus quinquestriatus hebraeus* which was purified using reverse phase HPLC.

An "intermediate" toxin has also been discovered which affects insect sodium channels in a manner very similar to the effect of alpha toxins on mammalian sodium channels. This neurotoxin was derived from a yellow scorpion *Leuirus quinquestriatus hebraeus*, Buthinae, Buthidae and is called herein LqhP35. The identification and purification of this toxin was described in copending patent application Ser. No. 07/286,002, Zlotkin et al., filed Dec. 19, 1988, and entitled "Toxin to Insects Derived from the Venom of the Scorpion *Leiurus quinquestriatus hebraeus*," which was incorporated herein by reference, now published by Citan et al., *Biochemistry*, 29:5941–5947 (1990), renamed "LqhαIT." The amino acid sequence for this neurotoxin is as follows: VRDAYIAKNY NCVYECFRDA YCNELCTKNG ASS-GYCQWAG KYGNACWCYA LPDNVPIRVP GKCR (SEQ. ID. NO:1).

Other toxins, purified from the venom of the chactoid scorpion, *Scorpio maurus palmatus*, can also be used in this invention. For example, SmpIT2, from the chactoid scorpion, *Scorpio maurus palmatus*, is a depressive insect toxin. Its purification is described in Lazarovici et al., *J. Biol. Chem.*, 257:8397–8404 (1982).

Still other toxins purified from the venom of the chactoid scorpion, *Scorpio maurus palmatus*, are SmpCT2 and SmpCT3, and crustacean toxins, whose purification has been described in Lazarovici, Ph.D. thesis (1980), Hebrew University, Jerusalem, "Studies on the Composition and Action of the Venom of the Scorpion *Scorpio maurus palmatus* (Scorpionidae)."

SmpMT is a mammalian toxin whose purification has been described in Lazarovici et al., *Comp. Biochem. Physiol.*, 71C:177–181 (1982).

Genetic Engineering of Insect Selective Toxins

This invention further comprises the genetic sequences coding for the insect selective toxins, expression vehicles containing the genetic sequences, hosts transformed therewith, the toxins produced by such transformed host expression, and uses for the toxin.

Secretion Signal Sequences

Another aspect of the present invention comprises the use of polypeptide sequences which are known to direct proteins to which they are operably linked into the cellular secretory pathway, or the genetic sequences encoding such polypeptide sequences, for the purpose of enhancing the effectiveness of toxins such as those above described when expressed, for example, in recombinant microbes. It is expected that secretion signal sequences from a wide variety of sources would be competent to carry out the function intended, because it is well-documented that the specificity of the signal recognition and processing apparatus in prokaryotic and eukaryotic cells is low. von Heijne, *J. Mol. Biol.*, 184:99–105 (1985). For the various purposes, however, it is likely that particular sources of secretion signal sequences will tend to be more useful than others.

For the purpose of producing recombinant baculoviruses which are effective in controlling insects, or which can be used in culture to infect cells and produce active toxins, the preferred secretion signal sequence is encoded by a nucleotide sequence, and when translated by the cellular translational apparatus, consists of any natural or artificial sequence of amino acids which can be demonstrated to promote secretion of an operably linked amino acid sequence, especially that set of amino acid sequences which are made up of the following four components: (1) a region at the amino terminal end which contains one or more basic amino acids, (2) a central region which is composed largely of hydrophobic amino acids, (3) a region at the carboxyl end which contains a larger number of polar amino acids than the central region, and (4) a site appropriate for recognition and cleavage by the signal peptidase enzyme (von Heijne, *Nucl. Ac. Res.*, 14:4683–4690 (1986)).

More preferred are secretion signal sequences derived from proteins of bacteria, yeast, fungi, or higher eukaryotes, including both animals and plants (for examples, see Watson, *Nucl. Ac. Res.*, 12:5145–5164 (1984). More preferred are secretion signal sequences from proteins of insect origin, for example those of cecropin B from Hyalophora cecropia (van Hofsten et al., *PNAS*, 82:2240–2243 (1985)), and the eclosion hormone from Manduca sexta (Horodyski et al., *PNAS*, 86:8123–8127 (1989)). Also preferred are the secretion signal sequences naturally associated with scorpion toxins, which can be determined by the analysis of mRNA, CDNA, or genomic DNA as described in Section I. More preferred is the natural secretion signal sequence of AaIT (Bougis et al., *J. Biol. Chem.*, 264:19259–19265 (1989)). Also preferred are signal sequences from those higher eukaryotes which have been the source of genes whose translated products are effectively secreted by recombinant baculovirus-infected cells, for example, mammals and plants. More preferred are the signal sequences encoded in genes whose translated products are effectively secreted by recombinant baculovirus-infected cells, for example, human colony stimulating factor I (Luckow et al., *Biotechnology*, 6:47–55 (1989)), human alpha-interferon (Id.), human beta-interferon (Id.), human interleukin-2 (Id.), French bean (*Phaeseolus vulgaris*) phaeseolin (Id.), and mouse interleukin-3 (Miyajima et al., *Gene*, 58:273–281 (1987)). Especially preferred are secretion signal sequences from proteins of *Bombyx mori*, for example, those of storage proteins 1 (Sakurai et al., *Nucl. Ac. Res.*, 16:7717–7718 (1988)) and 2 (Fujii et al., *J. Biol. Chem.*, 264:11020–11025 (1989)). Most preferred is the secretion signal sequence of bombyxin (Adachi et al., *J. Biol. Chem.*, 264:7681–7685 (1984)).

Also preferred are secretion signal sequences derived from the genes of scorpion toxins. More preferred is the secretion signal sequence of AaIT (Bougis et al., *J. Biol. Chem.*, 264:19259–19265 (1989)).

Expression of the Insect Selective Toxin and Its Functional Derivatives

The toxin encoding sequences, obtained through the methods described above, may be operably linked to an expression vector, and introduced into prokaryotic or eukaroytic cells in order to produce the toxin or its functional derivatives. The present invention pertains both to the intact toxin and to the functional derivatives of this toxin.

A "functional derivative" of the toxin is a compound which possesses a biological activity (either functional or structural) that is substantially similar to a biological activity of the toxin. The term "functional derivative" is intended to include the "fragments," "variants," "analogues," or "chemical derivatives" of a molecule. A "fragment" of a molecule such as the toxin is meant to refer to any polypeptide subset of the molecule. A "variant" of a molecule such as the toxin is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analog" of a molecule such as the toxin is meant to refer to a molecule substantially similar in function to either the entire molecule or to a fragment thereof. As used herein, a molecule is said to be a "chemical derivative" of another molecule when it contains additional chemical moieties not normally a part of the molecule.

Such moieties may improve the molecule's solubility, absorption, biological half-life, etc. Moieties capable of mediating such effects are disclosed in Remington's Pharmaceutical Sciences (1980). Procedures for coupling such moieties to a molecule are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of the toxin synthesis. Such regions will normally include those 5'-non-coding sequences involved with initiation of transcription and translation, such as the TATA box, capping sequence, CAAT sequence, and the like.

If desired, the non-coding region 3' to the genes sequence coding for the toxin may be obtained by the above-described methods. This region may be retained for its transcriptional termination regulatory sequences, such as termination and polyadenylation. Thus, by retaining the 3'-region naturally contiguous to the DNA sequence coding for the toxin, the transcriptional termination signals may be provided. Where the transcriptional termination signals are not satisfactorily functional in the expressed host cell, then a 3' region functional in the host cell may be substituted.

Two DNA sequences (such as a promoter region sequence and the toxin encoding sequence) are said to be operably linked if the nature of the linkage between the two DNA sequences does not (1) result in the introduction of a frame-shift mutation, (2) interfere with the ability of the promoter region sequence to direct the transcription of the toxin gene sequence, or (3) interfere with the ability of the toxin gene sequence to be transcribed by the promoter region sequence. Thus, a promoter region would be operably linked to a DNA sequence if the promoter were capable of effecting transcription of that DNA sequence. To express the toxin transcriptional and translational signals recognized by an appropriate host are necessary.

A preferred host is insect cells, for example, the Drosophila larvae. Using insect cells as hosts, the Drosophila alcohol dehydrogenase promoter can be used (Rubin, *Science*, 240:1453–1459 (1988)). Alternatively, baculovirus vectors can be engineered to express large amounts of the toxin in insect cells. Jasny, *Science*, 238:1653 (1987); Miller et al. in *Genetic Engineering* (1986), Setlow et al., eds., *Plenum*, Vol. 8:277–297. In a preferred embodiment, expression of the toxin in baculovirus vectors is enhanced by the presence of a signal sequence coding for a secretory peptide.

Expression of the toxin in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene (Hamer et al., *J. Mol. Appl. Gen.*, 1:273–288 (1982)); the TK promoter of Herpes virus (McKnight, *Cell*, 31:355–365 (1982)); the SV40 early promoter (Benoist et al., *Nature* (London), 290:304–310 (1981)); the yeast gal4 gene promoter (Johnston et al., *PNAS* (USA), 79:6971–6975 (1982); Silver et al., *PNAS* (USA), 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the toxin (or a functional derivative thereof) does not contain any intervening codons which are capable of encoding a methionine (i.e., AUG). The presence of such codons results either in a formation of a fusion protein (if the AUG codon is in the same reading frame as the toxin encoding DNA sequence) or a frame-shift mutation (if the AUG codon is not in the same reading frame as the toxin encoding sequence).

The toxin encoding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the toxin may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of mRNA. These elements may include splice signals, as well as transcription promoters, enhancers, and termination signals. cDNA expression vectors incorporating such elements include those described by Okayama, *Mol. Cel. Biol.*, 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, øVX. Such plasmids are, for example, disclosed by Maniatis et al. (*Molecular Cloning, A Laboratory Manual*, Cold Spring Harbor Press, Cold Spring Harbor, N.Y. (1982)) now updated by Sambrook et al. (2nd Ed. 1990). Bacillus plasmids include pC194, pC221, pT127, etc. Such plasmids are disclosed by Gryczan (*The Molecular Biology of the Bacilli*, Academic Press, N.Y. (1982), pp. 307–329). Suitable Streptomyces plasmids include pIJ101 (Kendall et al., *J. Bacteriol.*, 169:4177–4183 (1987)), and *Streptomyces* bacteriophages such as ø2C31 (Chater et al., *Sixth International Symposium on Actinomycetales Biology*, Akademiai Kaido, Budapest, Hungary (1986), pp. 45–54). Pseudomonas plasmids are reviewed by John et al. (*Rev. Infect. Dis.*, 8:693–704 (1986)), and Izaki (*Jpn. J. Bacteriol.*, 33:729–742 (1978)).

Preferred eukaryotic plasmids include BPV, vaccinia, SV40, 2-micron circle, etc., or their derivatives. Such plasmids are well known in the art (Botstein et al., *Miami Wntr. Symp.*, 19:265–274 (1982); Broach, *The Molecular Biology of the Yeast Saccharomyces: Life Cycle and Inheritance*, Cold Spring Harbor Laboratory, Cold Spring Harbor, N.Y., pp. 445–470 (1981); Broach, *Cell*, 28:203–204 (1982); Bollon et al., *J. Clin. Hematol. Oncol.*, 10:39–48 (1980); Maniatis, *Cell Biology: A Comprehensive Treatise*, Vol. 3, Gene Expression, Academic Press, N.Y., pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of the toxin, or in the production of a fragment of this toxin. This can take place in the transformed cells as such, or following the induction of these cells to differentiate (for example, by administration of bromodeoxyuracil to neuroblastoma cells or the like).

The expressed protein may be isolated and purified in accordance with conventional conditions, such as extraction, precipitation, chromatography, affinity chromatography, electrophoresis, or the like.

Use of the Insect-Selective Toxin to Improve Insecticidal Microbes.

In one embodiment of the present invention, the insect selective toxin alone or in combination with any of the enhancing compounds mentioned above is used to improve one or more insect control properties, such as to enhance the toxicity of insecticidal microbes, preferably to increase kill rate. The microbes useful in the present invention include baculoviruses, fungi and bacteria.

On the order of forty nuclear polyhedrosis viruses have been isolated from insect species. (See, for example, *Atlas of Invertebrate Viruses*, Adams and Bonami, editors, CRC Press, Inc., 1991). Various baculoviruses, including those that infect cotton bollworm, *Helicoverpa zea*, tobacco budworm, *Heliothis virescens*, Douglas fir tussock moth, *Orgia pseudotsugata*, gypsy moth, *Lymantria dispar*, alfalfa looper, *Autographa californica*, European pine fly, *Neodiprion sertifer*, and codling moth, *Laspeyresia pomonella*, have been registered as pesticides and all such baculoviruses from insect species are suitable for practicing the invention.

The preferred baculovirus for the present invention is the *Autographa californica* nuclear polyhedrosis virus (AcNPV). Introduction of an insect-selective toxin into the genome of such a baculovirus can significantly enhance the potency of such pesticide. Baculoviruses used can be hybrids with wider host ranges than the wild type viruses from which they are derived. For example, one of us coauthored an article "Host Range Expansion of *Autographa californica* Nuclear Polyhedrosis Virus (NPV) Following Recombination of a 0.6 kb-pair DNA Fragment Originating from *Bombyx mori* NPV," *Journal of Virology*, pp.

6234–6238 (1993) in which is described the isolation of a hybrid baculovirus with a range-expansion designated "eh2-AcNVP." Although the particular isolate described does have an expanded host-range, its virulence to Spodoptera cells seems to be lower than wild-type AcNPV, and thus this isolate seems not the best virus for the agricultural insect control uses described herein. Nevertheless, subsequent tests of this expanded host-range eh2-AcNPV in second instar larvae of *B. mori* found that the occluded form is orally infectious to these larvae, and produces typical viral symptomology in the infected hosts. Thus, host-range expanded baculoviruses (but that are more appropriately virulent than the particular eh2-AcNPV isolate described in the 1993 article) could be isolated by screening with cells such as SF-21 and BmN (see, for example, screenings described by Maeda, U.S. Pat. No. 5,266,314, issued Nov. 30, 1993) and these hybrids used as the recombinant baculovirus of the invention. Further, such a strategy should also permit viral mass production in the larvae of *B. mori* (which weigh up to 6 g) rather than the much smaller Noctuid larvae typically used for mass production of nuclear polyhedrosis viruses.

Numerous fungi are capable of infecting insects. Introduction of the insect-selective toxin into the genome of such fungi could enhance the potency as pesticides. For example, *Beauvaria bassania* and *Beauvaria brongniartii* have a wide host range and have been suggested as candidates for microbial pesticides (see review by Miller et al., *Science*, 219:715–721, 1983). Bacteria (other than *Bacillus thuringiensis*) that have been considered as insect control agents include *Bacillus popilliae, B. lentimorbus*, and *B. sphaericus*. Their potential as pesticides can be enhanced by improving their potency through the incorporation of an insect-selective toxin into their genome.

One embodiment of the present invention comprises insecticidal microbes, especially baculoviruses, which exhibit an improved insect control property, such as an enhanced toxicity to insects. The genome of the baculoviruses in this invention comprises a genetic sequence coding for an insect-selective protein neurotoxin isolated from venom, such as earlier disclosed.

In another embodiment of the present invention, methods are provided for preparing an insecticidal microbe with an improved insect control property, such as by enhancing the toxicity of an insecticidal microbe, by isolating a recombinant DNA molecule comprising a genetic sequence coding for an insect-selective protein neurotoxin isolated from venom, and introducing the recombinant DNA molecule into the genome of the insecticidal microbe.

The recombinant DNA molecule comprises a genetic sequence for an insect-selective protein neurotoxin isolated from venom, such as scorpion venom. The preferred insect-selective toxins of the present invention are those insect-selective toxins which, when the DNA coding sequence is inserted into the genome of a baculovirus, will result in a recombinant baculovirus having improved insecticidal properties. Preferred are the alpha, depressant and intermediate toxins. Most preferred are those insect-selective toxins having an amino acid sequence of from about 60 to about 70 amino acids in length. Especially preferred are the AaIT, LqhP35, LqhIT2, and LqqIT2 toxins. The most preferred insect-selective neurotoxin is the AaIT toxin.

The recombinant DNA molecule comprises regulatory sequences to effect the expression of the coding sequence. These regulatory sequences preferably include promoter sequences, untranslated leader sequences, and a signal sequence to promote the secretion of the toxin protein, once expressed.

The present invention also includes methods of producing insect selective toxins comprising preparing an expression vector which codes for the production of an insect-selective toxin, introducing the expression vector into the genome of an expression system host, and allowing the host to produce an expression supernatant. The supernatant may be extracted from the host and the insect-selective toxin may be isolated from the supernatant. Preferred hosts include *E. coli* and yeast. Especially preferred as the host are insect cells, either cultured or in living insects, which have been infected with a baculovirus containing a DNA sequence coding for the production of the insect-selective toxin.

Having now generally described this invention, the same will be better understood by reference to specific examples, which are included herein for purposes of illustration only, and are not intended to be limiting unless otherwise specified. Insect-selective toxins can be introduced into organisms such as a plant by genetic engineering techniques. Example A illustrates preparation of a plasmid derived vector useful for transforming plant tissue, since the AaIT toxin gene can be ligated into the BamHl site; however, Examples 1–8 illustrate construction and uses of the AaIT gene encoding toxin by inserting into two different baculoviruses so as to create recombinant baculoviruses, which can be used to infect insect cells.

EXAMPLE A

Construction of a Ti Plasmid-Derived Vector

The vector pCIB10 (Rothstein et al., *Gene*, 53:153–161 (1987)) is a Ti-plasmid-derived vector useful for transfer of the chimeric gene to plants via *Agrobacterium tumefaciens*. The vector was derived from the broad host range plasmid pRK252, which may be obtained from Dr. W. Barnes, Washington University, St. Louis, Mo. The vector also contains a gene for kanamycin resistance in Agrobacterium, from Tn903, and left and right T-DNA border sequences from the Ti plasmid pTiT37. Between the border sequences are the polylinker region from the plasmid pUC18 and a chimeric gene that confers kanamycin resistance in plants.

Figure 1:
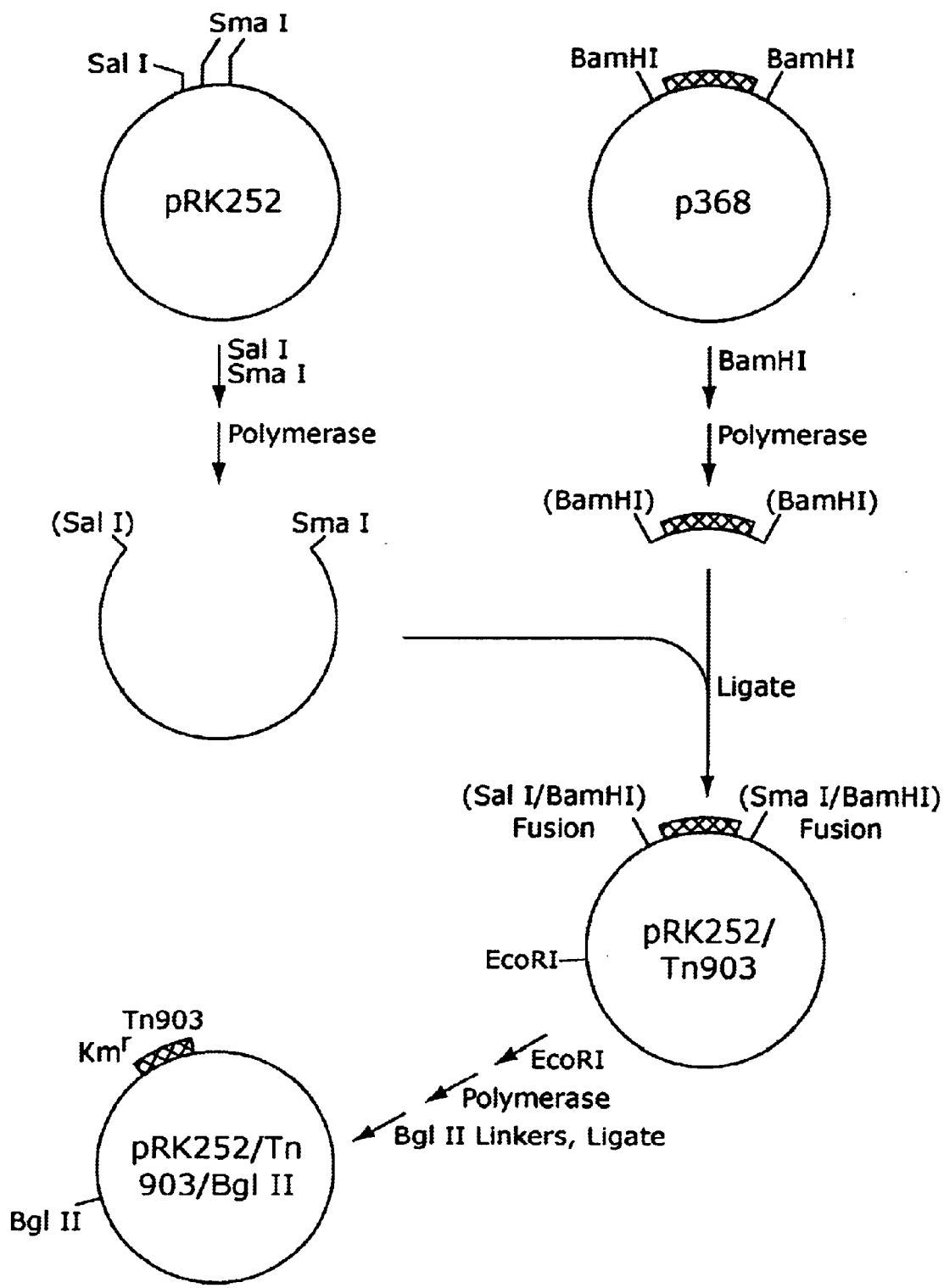
FIG. 1 shows the construction of pRK252/Tn903/BglII.

First, plasmid pRK252 was modified to replace the gene conferring tetracycline-resistance with one from the transposon Tn903 conferring resistance to kanamycin (Oka et al., *J. Mol. Biol.*, 147:217–226 (1981)), and was also modified by replacing the unique EcoRI site in pKR252 with a BglII site (see FIG. 1 for a summary of these modifications). Plasmid pRK252 was first digested with endonucleases SalI and SmaI, then treated with the large fragment of DNA polymerase I to create flush ends, and the large vector fragment purified by agarose gel electrophoresis. Next, plasmid p368, which contains Tn903 on an approximately 1050 bp BamHI fragment, was digested with endonuclease BamHI, treated with the large fragment of DNA polymerase, and an approximately 1050 bp fragment was isolated after agarose gel electrophoresis; this fragment contained the gene from transposon Tn903 which confers resistance to the antibiotic kanamycin (Oka et al., *J. Mol. Biol.*, 147:217–226 (1981)). Plasmid p368 has been deposited with ATdC, accession number 67700. Both fragments are then treated with the large fragment of DNA polymerase to create flush ends. Both fragments are mixed and incubated with T4 DNA ligase overnight at 15° C. After transformation into *E. coli* strain HB101 and selection for kanamycin resistant colonies, plasmid pRK252/Tn903 is obtained (see FIG. 1).

Plasmid pRK252/TN903 was digested at its unique EcoRI site, followed by treatment with the large fragment of *E. coli* DNA polymerase to create flush ends. This fragment was added to synthetic BglII restriction site linkers, and incubated overnight with T4 DNA ligase. The resulting DNA was digested with an excess of BglII restriction endonuclease and the larger vector fragment purified by agarose gel electrophoresis. The resulting fragment was again incubated with T4 DNA ligase to recircularize the fragment via its newly-added BglII cohesive ends. Following transformation into *E. coli* strain HB101, plasmid pRK252/Tn903/GblII was obtained (see FIG. 1).

Figure 2:
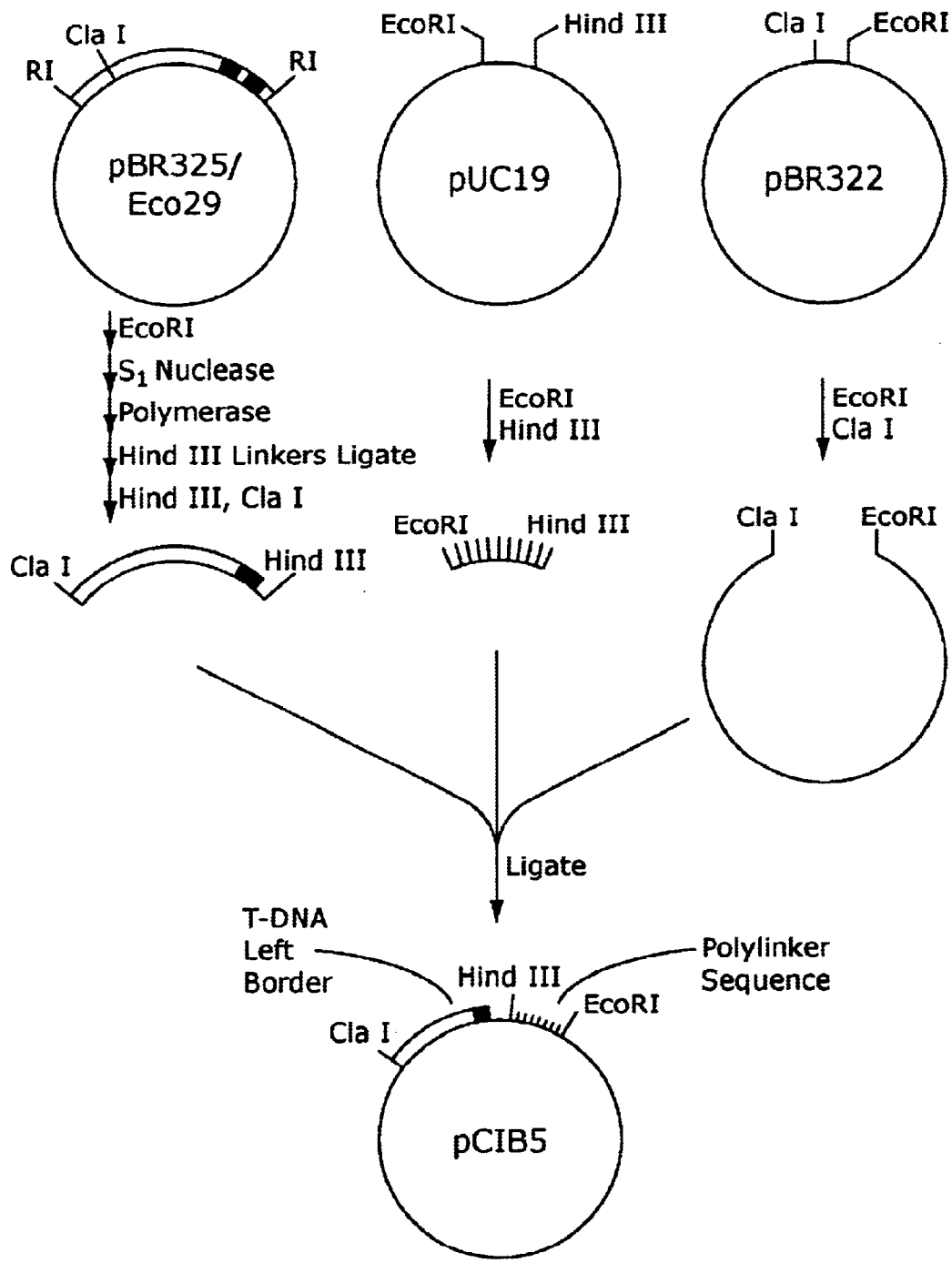
FIG. 2 shows the construction of pCIB 5.

A derivative of plasmid pBR322 was constructed which contains the Ti plasmid T-DNA borders, the polylinker region of plasmid pUC19, and the selectable gene for kanamycin resistance in plants (see FIG. 2). Plasmid pBR325/Eco29 contains the 1.5 kbp EcoRI fragment from the nopaline Ti plasmid pTiT37. This fragment contains the T-DNA left border sequence; Yadav et al., *Proc. Natl. Acad. Sci. USA*, 79:6322–6326 (1982). To replace the EcoRI ends of this fragment with HindIII ends, plasmid pBR325/Eco29 DNA was digested with EcoRI, then incubated with nuclease S1, followed by incubation with the large fragment of DNA polymerase to create flush ends, then mixed with synthetic HindIII linkers and incubated with T4 DNA ligase. The resulting DNA was digested with endonucleases ClaI and an excess of HindIII, and the resulting 1.1 kbp fragment containing the T-DNA left border was purified by gel electrophoresis. Next, the polylinker region of plasmid pUC19 was isolated by digestion of the plasmid DNA with endonucleases EcoRI and HindIII and the smaller fragment (approx. 53 bp) was isolated by agarose gel electrophoresis. Next, plasmid pBR322 was digested with endonuclease EcoRI and ClaI, mixed with the other two isolated fragments, incubated with T4 DNA ligase and transformed into *E. coli* strain HB101. The resulting plasmid, pCIB5, contained the polylinker and T-DNA left border in a derivative of plasmid pBR322 (see FIG. 2).

Figure 3:
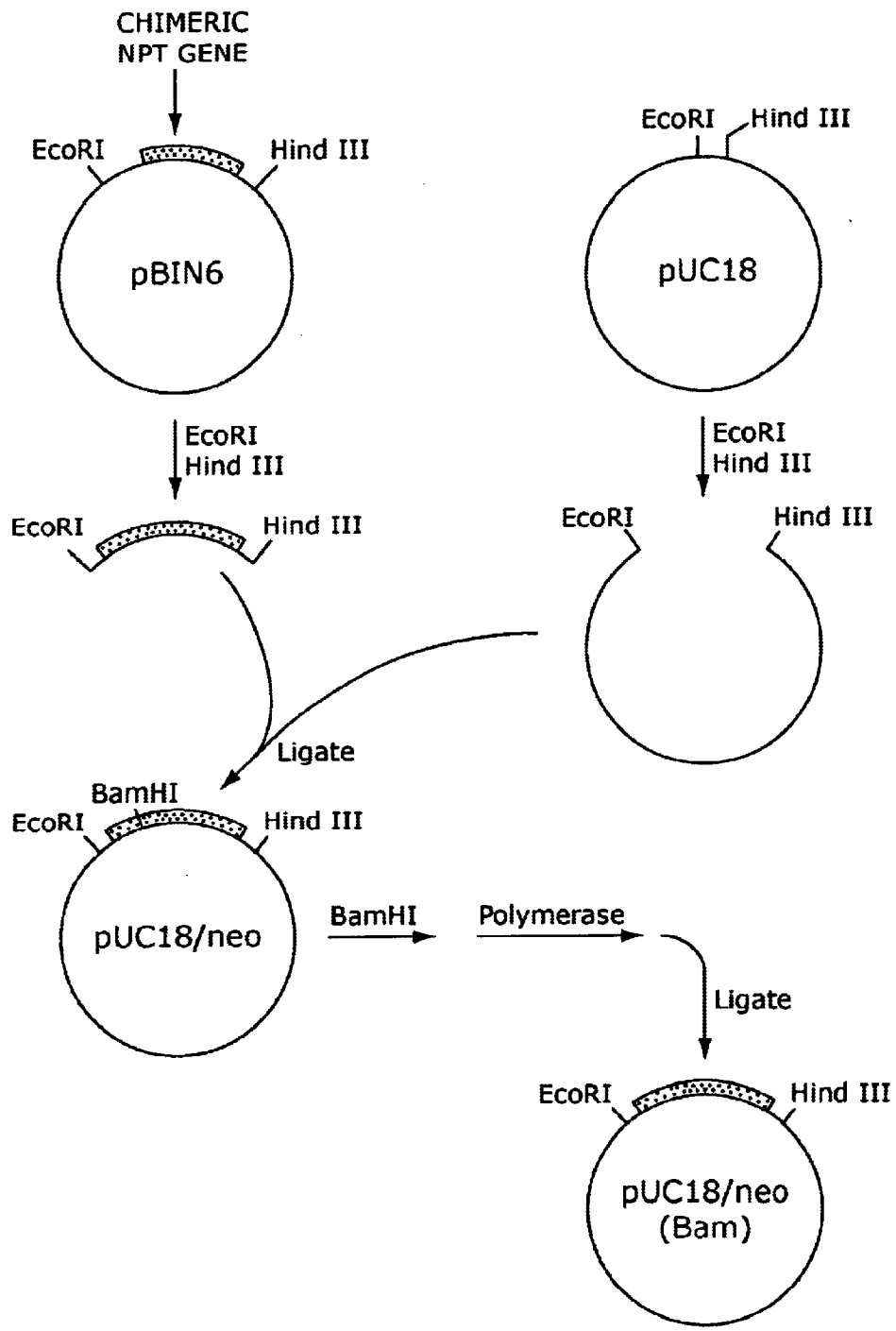
FIGS. 3 and 4 show the construction of PCIB 4.
Figure 4:
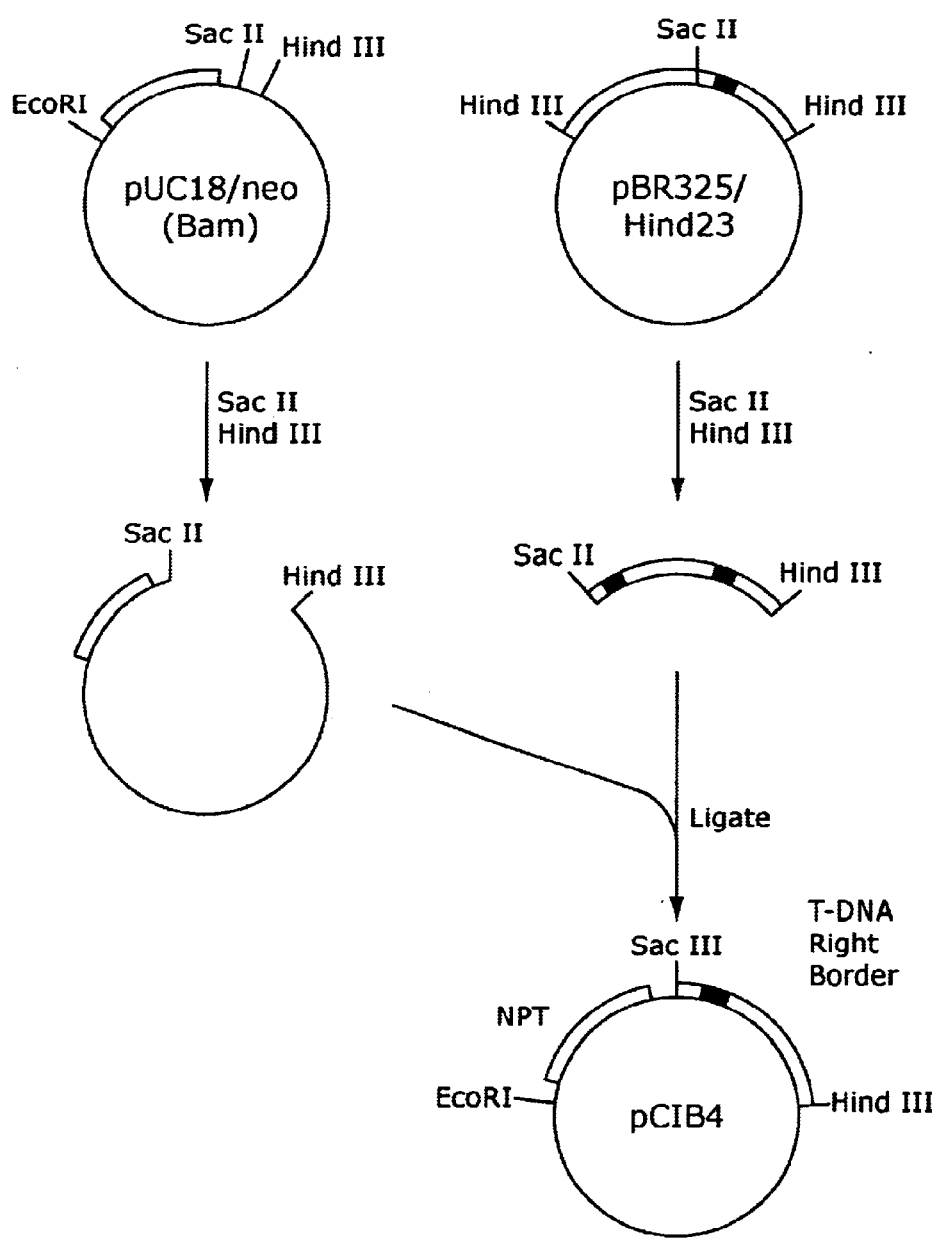

A plasmid containing the gene for expression of kanamycin resistance in plants was constructed (see FIGS. 3 and 4). Plasmid Bin6 was obtained from Dr. M. Bevan, Plant Breeding Institute, Cambridge, UK. This plasmid is described in Bevan, *Nucl. Acids Res.*, 12:8711–8721 (1984). Plasmid Bin6 DNA was digested with EcoRI and HindIII and the fragment approximately 1.5 kbp in size containing the chimeric neomycin phosphotransferase (NPT) gene was isolated and purified following agarose gel electrophoresis. This fragment was then mixed with plasmid pUC18 DNA which has been cleaved with endonucleases EcoRI and HindIII. Following incubation with T4 DNA ligase, the resulting DNA was transformed into *E. coli* strain HB101. The resulting plasmid is called pUC18/neo. This plasmid DNA contains an unwanted BamHI recognition sequence between the neomycin phosphotransferase gene and the terminator sequence for nopaline synthase; see Bevan, *Nucl. Acids Res.*, 12:8711–8721 (1984). To remove this recognition sequence, plasmid pUC18/neo was digested with endonuclease BamHI, followed by treatment with the large fragment of DNA polymerase to create flush ends. The fragment was then incubated with T4 DNA ligase to recircularize the fragment, and is transformed into *E. coli* strain HB101. The resulting plasmid, pUC18/neo(Bam) has lost the BamHI recognition sequence.

The T-DNA right border sequence was then added next to the chimeric NPT gene (see FIG. 4). Plasmid pBR325/Hind23 contains the 3.4 kbp HindIII fragment of plasmid pTiT37. This fragment contains the right T-DNA border sequence; Bevan et al., *Nucl. Acids Res.*, 11: 369–385 (1983). Plasmid pBR325/Hind23 DNA was cleaved with endonucleases SacII and HindIII, and a 1.0 kbp fragment containing the right border was isolated and purified following agarose gel electrophoresis. Plasmid pUC18/neo (Bam) DNA was digested with endonucleases SacII and HindIII and the 4.0 kbp vector fragment was isolated by agarose gel electrophoresis. The two fragments were mixed, incubated with T4 DNA ligase and transformed into *E. coli* strain HB101. The resulting plasmid, pCIb4 (shown in FIG. 4), contains the T-DNA right border and the plant-selectable marker for kanamycin resistance in a derivative of plasmid pUC18.

Figure 5:
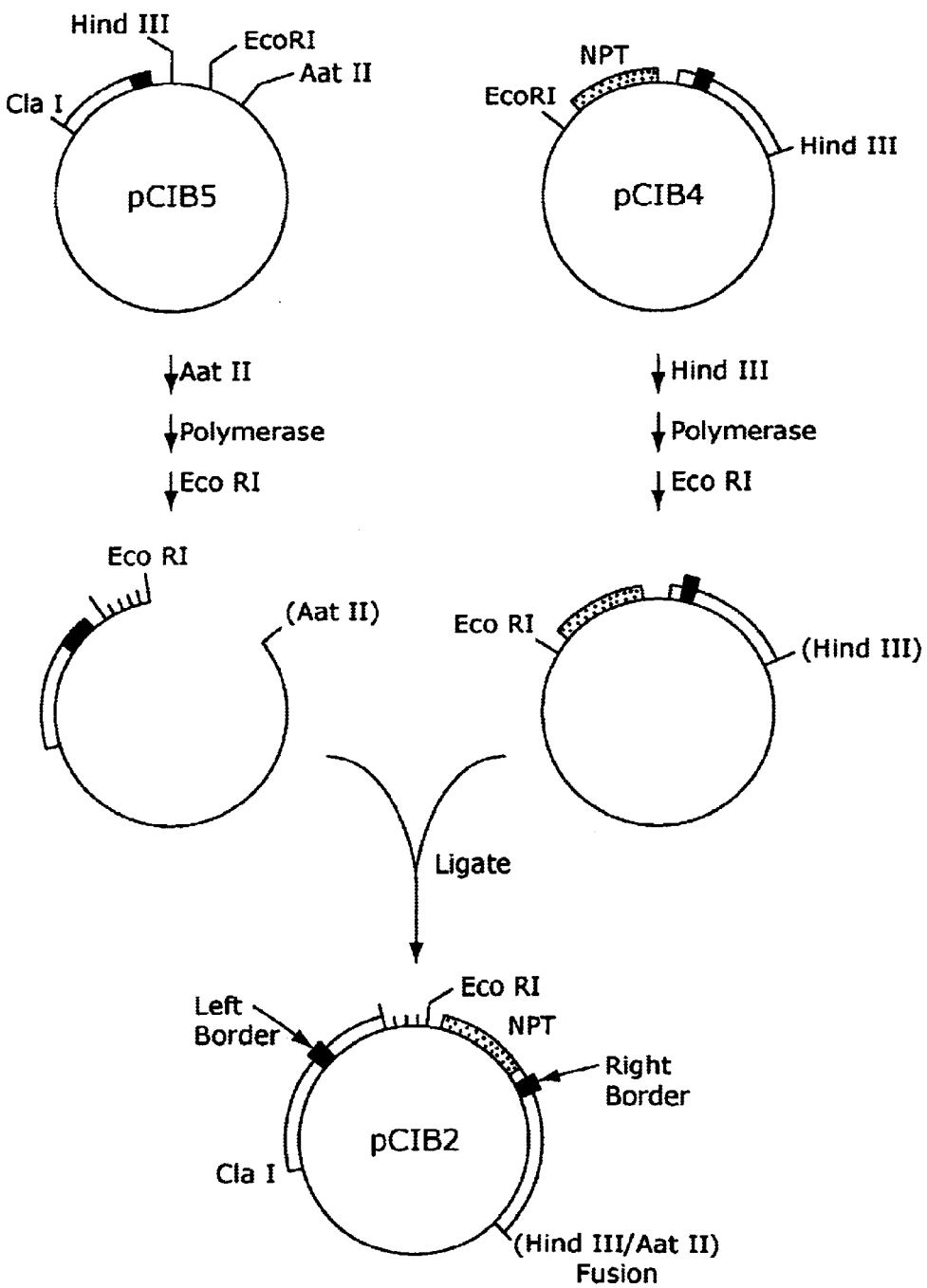
FIG. 5 shows the construction of PCIB 2.

Next a plasmid was constructed which contains both the T-DNA left and right borders, with the plant selectable kanamycin resistance gene and the polylinker of pUC18 between the borders (shown in FIG. 5). Plasmid pCIB4 DNA was digested with endonuclease HindIII, followed by treatment with the large fragment of DNA polymerase to create flush ends, followed by digestion of endonuclease EcoRI. The 2.6 kbp fragment containing the chimeric kanamycin-resistance gene and the right border of T-DNA was isolated by agarose gel electrophoresis. Plasmid PCIB5 DNA was digested with endonuclease AatII, treated with T4 DNA polymerase to create flush ends, then cleaved with endonuclease EcoRI. The large vector fragment was purified by agarose gel electrophoresis, mixed with the pCIB4 fragment, incubated with T4 DNA ligase, and transformed into *E. coli* strain HB101. The resulting plasmid, pCIB2 (shown in FIG. 5) is a derivative of plasmid pBR322 containing the desired sequences between the two T-DNA borders.

Figure 6:
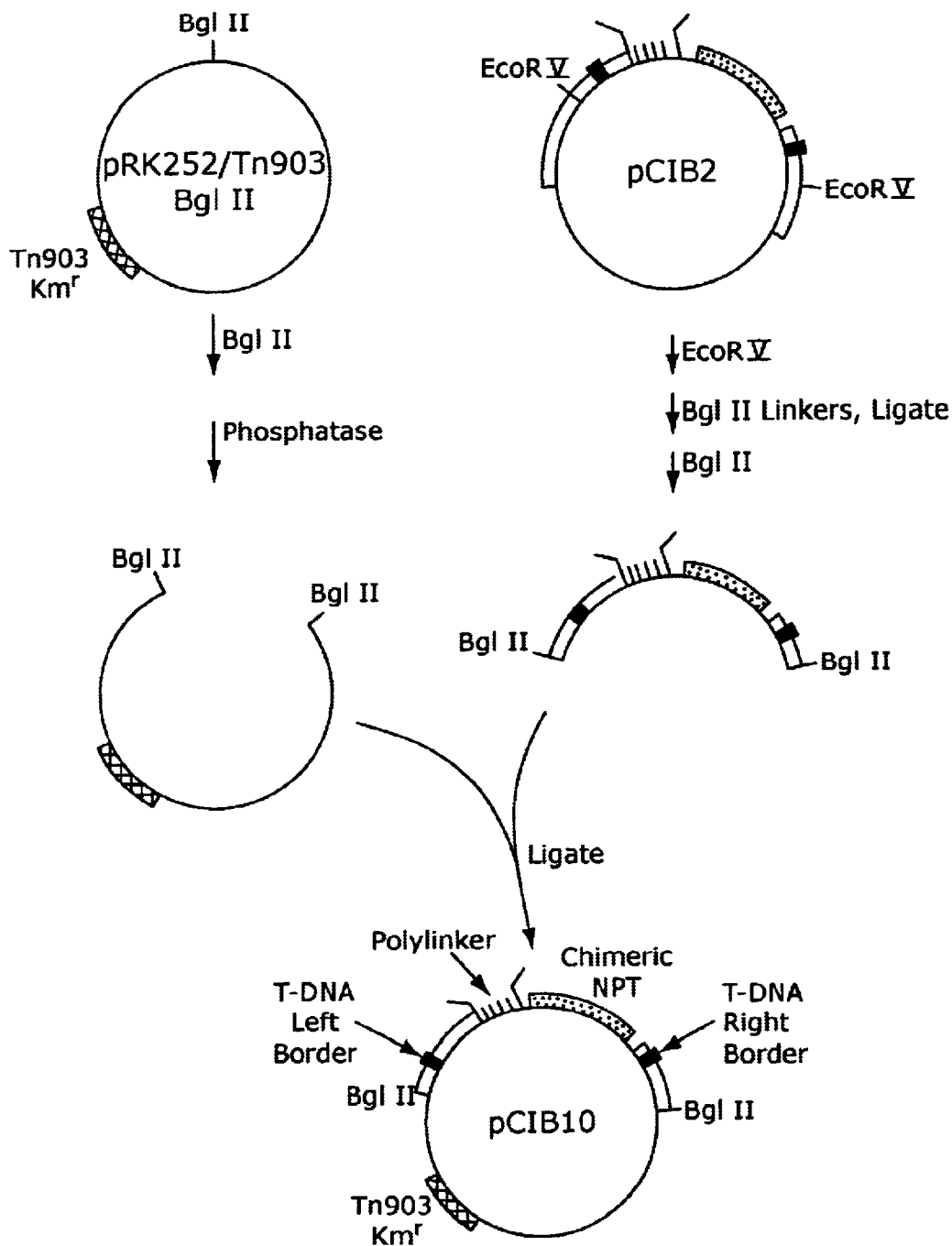
FIG. 6 shows the construction of PCIB 10, a broad host range plasmid containing T-DNA borders and a gene for plant selection.

The following steps complete construction of the vector pCIB710, and are shown in FIG. 6. Plasmid pCIB2 DNA was digested with endonuclease EcoRV, and synthetic linkers containing BglII recognition sites were added as described above.

After digestion with an excess of BglII endonuclease, the approximately 2.6 kbp fragment was isolated after agarose gel electrophoresis. Plasmid pRK252/Tn903/BglII, described above (see FIG. 1), was digested with endonuclease BglII and then treated with phosphatase to prevent recircularization. These two DNA fragments are mixed, incubated with T4 DNA ligase and transformed into *E. coli* strain HB101. The resulting plasmid was the completed vector, pCIB10.

Plasmid pCIB10 comprises T-DNA borders containing a plant expressible neomycin phosphotransferase gene and convenient restriction endonuclease sites for insertion of other chimeric genes within the T-DNA borders.

EXAMPLE 1

A. Synthesis of Genes Encoding Insect-Selective Toxins Purification of Insect-Selective Toxins The purification of several insect toxins has already been described in several works by Zlotkin (Zlotkin, supra; Lester, supra). An alternative method which allows purification with high recoveries from limited amounts of venom is to use high performance liquid chromatography. This technique is exemplified in the purification of LqhIT2.

For purification of LqhIT2, lyophilized *Leiurus quinquestriatus hebraeus* venom (Sigma) is extracted three times using 0.5 ml water/20 mg venom. The water extracts are combined and subjected to ion-exchange chromatography on sulfoethylaspartamide HPLC column (Nest Group). The extract is applied to the column previously equilibrated in 5 mM $KPO_4$, pH 3.0 in 25% acetonitrile and the column eluted with a gradient from 0 to 0.5 M KC1 in the same buffer over 60 minutes. Individual fractions are desalted and further separated by reverse phase chromatography on a Vydac C-8 column equilibrated in 0.1% trifluoroacetic acid and eluted with a 75 minute gradient from 0 to 70% B (B=acetonitrile:isopropanol 1:1 in 0.1% trifluoroacetic acid). Individual fractions are tested for toxicity to insects by injection into Sarcophaga or Heliothis larvae as described by Zlotkin et al. (1985).

B. Amino Acid Sequencing of Insect Toxins

The insect toxin is reduced by incubating samples in 6M guanidine HCl, 1 M Tris HCl, pH 8.6, 10 mM EDTA, 20 mM dithiothreitol for 1 hour at 37° C. 4-vinylpyridine (Sigma) is added to 50 mM and incubation continued at room temperature for 1 hour. The modified protein is desalted on a Vydac C-8 column as described above. Peptides are produced by enzymatic digestion with trypsin, Lys-C, or Glu-C or by partial acid hydrolysis following standard procedures (Allen, *Sequencing of Proteins and Peptides*, North-Holland Pub. Co., Amsterdam, pp. 43–71 (1981)). Peptides are separated by reverse phase HPLC prior to sequencing. The amino acid sequences of the intact toxin and the individual peptides are determined by automatic Edman degradation using a Model 470A Protein Sequencer (Applied Biosystems, Foster City, Calif.) equipped with an on-line reverse phase HPLC for analysis of the phenylthiohydantoin derivatives of the amino acids and a Model 900 data analysis system. FIG. 7 shows the regions sequenced. The sequence determined for the LqhIT2 toxin is: DGY-IKRRDGC KVACLIGNEG CDKECKAYGG SYGY-CWTWGL ACWCEGLPDD KTWKSETNTCG (SEQ. ID. NO:2). Sequences of other insect toxins are determined using the same techniques are provided in FIG. 8.

C. Synthesis of Gene Encoding Insect Toxin

Since the insect toxins are small proteins (<80 amino acids), a gene encoding a toxin may be constructed by DNA synthesis. The following describes the synthesis of a gene which encodes AaIT, the *Androctonus australis* insect toxin.

The published sequence (Darbon et al., *Int. J. Peptide Prot. Res.*, 20:320–330 (1982)) is back-translated using the genetic code. In some cases alternative codons may be selected to facilitate synthesis and/or provide convenient restriction sites. Translational stop and start signals are added along with BamHl linkers at both ends for convenience in subsequent manipulations. This process yields the sequences shown in SEQ. ID. NO:10 and SEQ. ID. NO:11 (FIG. 9).

Oligonucleotides corresponding to the regions 1–20 (SEQ. ID. NOS:12–33) are synthesized using a Model 380A DNA synthesizer (Applied Biosystems, Foster City, Calif.) with beta-cyanoethyl chemistry).

The gene is assembled in the following steps:

(1) Set up the following reaction mixtures containing 40 pmoles of the indicated fragments.

A. Fragments 2, 12, 13

B. Fragments 3, 4, 14, 15

C. Fragments 5, 6, 7, 16, 17, 18

D. Fragments 8, 9, 19, 20

E. Fragments 10, 11, 21

(2) A 5' PO4 is added to the 5' ends of the fragments in each mixture by using T4 polynucleotide kinase according to the method described by Maniatis et al., supra.

(3) After removal of excess reagents by phenol/chloroform extraction, chloroform extraction, and ethanol precipitation, the precipitate of each mixture which contains the phosphorylated fragments is dissolved in T4 ligase buffer. 40 pmoles of fragment 1 is added to mixture A and 40 pmoles of fragment 22 is added to mixture E. The mixtures are heated to 85° C., then slow-cooled to 15° C. and maintained at 15° C. for at least 4 hours to allow fragments to anneal.

(4) Ligation. ATP is added to 1 mM along with T4 ligase and incubation is continued for 4 hours. Reagents are removed by extraction and precipitation as in step 1. To check for the efficacy of the reaction, an aliquot of the products is analyzed on a 10–15% acrylamide gel. If necessary, the desired band is purified from each reaction mixture by preparative gel electrophoresis and recovered from the gel. Contaminates are again removed by precipitation.

The following band sizes are obtained from the first set of ligations:

| | |
|---|---|
| Mixture A: | 49 base pairs |
| Mixture B: | 45 base pairs |
| Mixture C: | 65 base pairs |
| Mixture D: | 45 base pairs |
| Mixture E: | 46 base pairs |

(5) The products from the first ligations of A and B are mixed in reaction F. Products from ligations D and E are mixed for reaction G. Steps three and four are repeated on mixtures F and G. This results in a 89 base pair fragment from reaction F and an 86 base pair fragment from reaction G.

(6) The purified fragments from reactions F, G, and C are mixed together and steps three and four are repeated to give the final gene of 230 base pairs with BamHl ends. The final sequence is shown in SEQ. ID. NO:34 (FIG. 9c). This purified fragment is used for ligation into the BamHl site of appropriate vectors.

(7) To amplify the DNA, the purified fragment is ligated into the BamHl site of pUC18 and cloned in a suitable *E. coli* host. The DNA sequence of the insert is confirmed using standard sequencing methodology.

EXAMPLE 2

Enhancement of Insecticidal Activity of Baculoviruses by Incorporation of Gene Encoding for AaIT Toxin A. Construction of PCIB4223 (Bombyxin signal seguence-AaIT in baculovirus transfer vector)

A DNA fragment containing the signal sequence of the *Bombyx mori* protein bombyxin (Adachi et al., *J. Biol. Chem.*, 264:7681–7685 (1989)) is produced by annealing and extending the primers SV69A23 (TGTTGACACC CACATTACTG TTGACAACAT TAATGC, SEQ. ID. NO:35) and SV70A23 (TAGAGCTCAT GAAGATACTC CTTGCTATTG CATTAA, SEQ. ID. NO:36) using the GeneAmp kit (Perkin-Elmer Cetus) and standard conditions for PCR amplification.

The reaction product is a 65 bp fragment composed of the bombyxin signal sequence with the addition of a SacI restriction site at its 5' end.

A DNA fragment containing the AaIT gene is produced using the primers SV65A23 (AATCTAGAGG ATC-CTAGTTG ATGATAGTAG TGTCGC, SEQ. ID. NO:37) and SV68A23 (GTAATGTGGG TGTCAACAAA AAAAAACGGC TACGCT, SEQ. ID. NO:38) to amplify by PCR a fragment from the AaIT clone described in Example 1. The reaction product is a 247 bp fragment with 18 bp of the bombyxin signal sequence attached in correct reading frame to the 5' end of the AaIT gene sequence. The AaIT sequence is modified to include a penultimate isoleucine codon that is not included in the original clone but is indicated in the protein sequence published in Darbon et al., *Int. J. Pep. Prot. Res.* 20:320–330, 1982. This fragment has an XbaI restriction site at its 3' end.

The two products above are precisely fused using an overlapping PCR strategy that uses the bombyxin sequence contained in both to initiate the reaction, and then uses the two flanking primers, SV65A23 and SV70A23, to amplify the fused product (Higuchi et al., *NAR* 16:7351–7367, 1988). The final product is a 291 bp fragment containing the bombyxin signal sequence fused to the AaIT sequence and having SacI and XbaI restriction sites at its 5' and 3' ends, respectively. This product [Bs-AaIT] is cut with SacI and XbaI (NEB) and isolated by electrophoresis through 2.5% NuSieve GTG agarose (FMC Bioproducts). The appropriate fragment is excised, melted at 65° C., and approximately 1% is used directly in a standard ligation reaction with 50 ng of SacI/XbaI digested pBK283 (Maeda, "Gene Transfer Vectors of a Baculovirus, *Bombyx mori* Nuclear Polyhedrosis Virus, and Their Use for Expression of Foreign Genes in Insect Cells," in *Invertebrate Cell System Applications*, Vol. I, J. Mitsuhashi, ed., CRC Press, Boca Raton, Fla., 1990). Ten percent of the ligation mix is transformed into *E. coli* strain HB101 and transformants are selected on L-broth containing 100 $\mu$g/ml ampicillin. Individual colonies are picked and screened by standard miniprep/restriction analysis and the correct clone is amplified using a large scale alkaline lysis plasmid prep procedure. Dideoxy sequencing is performed to verify the absence of PCR-introduced mutations. The correct clone is designated pCIB4223, which has the sequence (SEQ. ID. NO:39) shown by FIG. 13. pCIB4223 has been deposited with the American Type Culture Collection in Rockville, Md. and has been designated with the accession number ATCC 40906.

Thus, in one embodiment of the present invention, a synthetic gene encoding AaIT behind a secretion signal sequence from the silkworm neuropeptide bombyxin (Adachi et al., *J. Biol. Chem.*, 264:7681 (1989)) is constructed and inserted into a transfer vector of *Bombyx mori* nuclear polyhedrosis virus (BmNPV), pBK273, after the strong polyhedrin gene promoter. Three $\mu$g of the resulting recombinant plasmid pBmAaIT and two $\mu$g of BmNPV DNA are cotransfected into BmN cells. A recombinant virus, BmAaIT, lacking polyhedra production, is isolated by a plaque assay from the cotransfected culture supernatant by the method described in Maeda et al., *Nature*, 315:592 (1985); and Maeda, in Mitsuhashi (ed.), *Invertebrate Cell System and Applications*, vol. II (CRC Press, Boca Raton, Fla., 1989) pp. 167–181. When BmN cells are separately infected with BmAaIT, BmDH5, carrying the diuretic hormone gene3, and a control BmM14 with a deletion in the polyhedrin gene, all infections show the same cytopathic effects. BmM14 was constructed by homologous recombination of BmNPV and a plasmid containing a deletion (between 70 and 166 nucleotides from the translational initiation site) in the polyhedrin coding area generated by Bal31 digestion, as described in Maeda et al., *Nature*, 315:592 (1985). The deletion in the BmM14 polyhedrin gene caused production of a major polypeptide similar to polyhedra, but uncrystallized.

The physiological and insecticidal effects of BmAaIT are examined in the silkworm, *B. mori*, by the method described in Maeda et al. (1985) and Maeda (1989), above. When second instar larvae are injected with $10^5$ p.f.u. of virus, they show dramatic changes in behavior at about 40 hours post injection. The larvae show continuous rotations of the head, dorsal arching, and shaking of the body. All larvae stop feeding between 45 to 55 hours post injection and do not move, although they are still able to respond to prodding. All larvae die by 60 hours post injection. This is approximately a 40% increase in the speed of insect killing compared to the control BmM14 virus. As reported in Maeda, *Biochem. Biophys. Res. Commun.*, 165:1177 (1989), infection with BmDH5 virus causes about a 20% increase in the speed of killing, but the larvae infected with BmDH5 do not show any apparent changes in behavior.

To confirm the production of active AaIT peptide in infected silkworm larvae, hemolymph at 55 hours post-injection is injected into larvae of the blow fly, *Sarcophaga falculata*. Symptoms following injection occurred immediately and are similar to those induced by AaIT purified from venom. However, hemolymph from larvae infected with control BmM14 virus produces no acute symptoms upon injection. A rough estimate based upon this biological assay indicates that the hemolymph contained 5 $\mu$g/ml of toxin. The expression of the AaIT gene in infected 5th instar larvae is also confirmed by immunoblot of hemolymph samples taken at various times after infection. An immunoreactive band which co-migrated with authentic AaIT is detected in the 48 hour and 55 hour samples showing that the expressed material and the toxin purified form venom have similar specific activity. The amount of material in the 55 hour sample is about 5 $\mu$g/ml. The estimated molecular weight of the toxin is identical with that of the native toxin, indicating the correct cleavage of the heterologous signal sequence in insect larvae and secretion of the peptide toxin.

A recombinant BmNPV construct without the signal sequence does not secrete the peptide efficiently, demonstrating the necessity of the signal sequence for secretion. The DNA fragment containing the AaIT coding sequence was preceded by the sequence GAGCTCGAAT TCATG (SEQ. ID. NO:40) containing a SacI site and methionine for the transcriptional start signal without any insertion of nucleotides. This AaIT gene without a signal sequence was transferred into pBE283. The resultant plasmid was cotransfected with BmNPV T3 DNA into BmN cells and a recombinant BmNPV was isolated as described in Maeda, in Mitsuhashi (ed.), *Invertebrate Cell System and Applications*, Vol. II (CRC Press, Boca Raton, Fla., 1989) pp. 167–181. Larvae infected with this virus show paralytic symptoms at 60 hours p.i., but the time to death is similar to that caused by the control virus.

To determine whether or not the effects of the BmAaIT virus are caused directly by the expressed scorpion toxin, native scorpion toxin is purified by HPLC from commercially obtained venom (Sigma, Latoxan) and injected into second instar silkworm larvae (0.6 $\mu$l per 5–10 mg larva). Doses over 300 ng cause death in most larvae within 24 hours with onset of symptoms at 30 min post injection. Doses of 12–60 ng cause effects similar to infection with BmAaIT virus in more than half of the larvae within 24 hours; however, these larvae recover within 48 hours. Low doses (less than 6 ng) have no apparent effects. The abnormal behavior of larvae injected with the native toxin is the same as that observed following infection with BmAaIT. The sensitivity of the silkworm to AaIT is comparable to that of the cutworm, *Spodoptera littoralis*, for which de Dianous et al. (1987) reported an $LD_{50}$ of 130 ng/10 mg body weight. These data indicate that the BmNPV-silkworm system is useful for screening toxin genes for pest control. This system may be useful as a new approach in characterizing neurotoxin molecules and their effects in in vivo systems.

B. Preparation of Recombinant Baculovirus Carrying the BS-AaIT Gene.

The pCIB4223 transfer vector is used to prepare a recombinant *Bombyx mori* nuclear polyhedrosis virus carrying the Bs-AaIT gene as described by Maeda, "Gene transfer vectors of a baculovirus, *Bombyx mori* nuclear polyhedrosis virus, and their use for expression of foreign genes in insect cells", In *Invertebrate Cell System Applications*, Vol. I, J. Mitsuhashi, ed., CRC Press, Boca Raton, Fla., 1990).

C. Infection of *Bombyx mori* Larvae

*Bombyx mori* larvae are infected with the recombinant virus. Infection of 2nd, 3rd, 4th or 5th instar larvae leads to death of all insects 48–55 hours after infection. The time to death of insects infected with virus lacking the AaIT gene is 5 days. Insects infected with the Bs-AaIT recombinant virus show abnormal behaviors with spastic contractions and arching starting about 40 to 50 hours after injection, then become immobile before death. This set of symptoms, which is consistent with a neurotoxic effect, is not observed with the control virus. Data from a typical experiment is shown in Table I below.

TABLE I

Effect of Various Recombinant Baculoviruses on Third Instar Bombyx mori Larvae

| Virus Hours post Infection | Bs-AaIT[a] Wt. | Condition | M14[b] Wt. | Condition | Uninfected Wt. | Condition |
|---|---|---|---|---|---|---|
| 0 | 25.9 | Healthy | 50.1 | Healthy | 23.4 | Healthy |
|  | 26.2 | Healthy | 25.1 | Healthy | 25.2 | Healthy |
|  | 40.1 | Healthy | 24.5 | Healthy | 25.2 | Healthy |
|  | 50.2 | Healthy | 45.5 | Healthy | 31.3 | Healthy |
|  | 32.4 | Healthy | 30.1 | Healthy | [c] | Healthy |
| 21 | 37.8 | Healthy | 95.6 | Healthy | 61.7 | Healthy |
|  | 59.5 | Healthy | 53.7 | Healthy | 33.9 | Healthy |
|  | 99.5 | Healthy | 49.8 | Healthy | 47.0 | Healthy |
|  | 84.2 | Healthy | 43.7 | Healthy | 33.0 | Healthy |
|  | 55.3 | Healthy | 47.5 | Healthy | 89.0 | Healthy |
| 44 | 13.1 | alive | 97.8 | alive | 55.8 | alive |
|  | 11.0 | alive | 54.2 | alive | 51.6 | alive |
|  | 73.0 | alive | 55.9 | alive | 41.2 | alive |
|  | 71.2 | alive | 50.8 | alive | 71.4 | alive |
|  | 48.2 | alive | 63.6 | alive | 100.5 | alive |
| 51 | 2 arching 1 off diet 2 restless | | all healthy | | all healthy | |
| 53 | all arching none feeding | | all healthy all feeding | | all healthy all feeding | |
| 65 | all dead | | all alive | | all alive | |
| 86 |  | | 2 dead | | all alive | |
| 89 |  | | 3 dead | | all alive | |
| 95 |  | | all dead | | all alive | |

[a]Recombinant virus carrying Bs-AaIT gene
[b]Recombinant virus carrying a gene for juvenile hormone esterase, used as control
[c]Not recorded

EXAMPLE 3

Construction of an ACNPV Recombinant Baculovirus Containing the Gene Encoding AaIT.

In addition to *Bombyx mori* nuclear polyhedrosis virus (BmNPV) earlier described, *Autographa californica* nuclear polyhedrosis virus (AcNPV) was constructed for use as a recombinant baculovirus with enhanced insecticidal activity according to the present invention. Several transfer vectors of AcNPV are available for expression of foreign genes in agricultural pest insects including *Spodoptera exignia*, *Spodoptera fungiporda*, *Heliothis zea*, *Heliothis armigen*, *Heliothis virescens*, *Trichoplusia ni*, and related insects. Miller, *Ann. Rev. Microbiol.*, 42:177–199 (1988). Some of these vectors can be used for insertion of foreign genes without disrupting the original polyhedrin gene. Recombinant AcNPVs produced by these transfer vectors will produce polyhedral inclusion bodies as well as foreign gene products. Recombinant viruses having polyhedral inclusion bodies are especially preferred for their ability to infect an insect orally, which is the natural mode of infection of insects in the field.

Among the transfer vectors which can be used for expression of insect toxin genes in AcNPV is pAcUW(B), Weyer et al., *J. Gen. Virol.*, 71:1525–1534 (1990). The pAcUW(B) transfer vector contains the original polyhedrin gene with the original promoter and an insertion site (BglII) for expression of the foreign genes after the p10 promoter. The insect toxin gene is then inserted at the BglII site by ligation, and its orientation is checked by double digestion with restriction enzymes or by direct sequencing. For example, the AaIT toxin gene in the transfer vector pBK283, which has been designated pCIB4223, is digested with SacI and XbaI to excise the complete AaIT gene including a signal sequence of Bombyxin for secretion. The cleaved AaIT toxin gene is inserted into pTZ18R (Pharmacia), which is similar to a pUC plasmid, at the SacI and XbaI sites. The resultant plasmid is cleaved with SacI and a synthesized oligomer (5'-CGGATCCGATCG-3', SEQ. ID. NO:41) is inserted to generate BamHI site. The insertion of this oligomer is confirmed by screening with BamHI for the fragment containing the AaIT gene; the correct plasmid has a BamHI site due to the inserted oligomer and the BamHI site between the stop codon of the AaIT gene and XbaI site used for construction. For the insertion of the AaIT gene, the pAcUW(B) is cleaved with BglII. Cleaved pAcUW(B) and the AaIT toxin gene fragment cleaved with BamHI of the constructed plasmid are then ligated and transformed into *E. coli*, JM101. The correct plasmid containing the AaIT gene is about 10–12 kb long with one SacI site, but no BglII site. The direction of the inserted AaIT gene is confirmed by double digestion with SacI (5' end of the AaIT gene) and BamHI (within the coding sequence of the polyhedrin gene). A recombinant transfer vector derived from pAcUW(B) carrying the AaIT gene in the correct orientation has a fragment of about 1.6 kbp while the plasmids with insertions in opposite direction have a fragment of about 1.3 kbp.

A recombinant AcNPV is obtained by cotransfection of this recombinant transfer vector and viral DNA of AcNPV, which lacks production of the polyhedral protein (e.g., a virus with a deletion in the polyhedral gene coding sequence). The cotransfection is performed by the method described in Example 2A above. Recombinant viruses are screened by looking for viruses producing polyhedral inclusion bodies since the transfer vector pAcUW(B) has the polyhedrin gene with the original promoter. Confirmation of the insertion of the foreign gene is performed by Southern blot analysis. The recombinant virus is propagated in Sf cells and the occlusion bodies are collected and purified from the infected cells by centrifugation and washing with distilled water. Polyhedral inclusion bodies containing recombinant viruses carrying the AaIT gene are mixed in diet and larvae are allowed to feed. The effects of the recombinant baculovirus are measured in accordance with the data of Table I above. In all species tested, the speed of kill significantly increased.

Injection of *Manduca sexta* with Recombinant AcNPv Containing the Gene for AaIT.

When *Manduca sexta* larvae are infected with the recombinant AcNPV containing the AaIT gene, larvae typically show symptoms between 60 to 72 hours post-injection and are functionally dead in 4 to 5 days. No larvae injected with wild-type AcNPV are dead at this time. Control larvae injected with wild-type AcNPV die 7 to 8 days post-injection.

Oral Activity of Recombinant AcNPV Virus Containing the Gene for AaIT.

*Heliothis virescens* larvae are fed 1000–5000 occlusion particles of the recombinant AcNPV containing the AaIT gene (AcNPV-AaIT) mixed in diet. Symptoms including spastic contractions and cessation of feeding appear in all larvae fed AcNPV-AaIT virus by 75 hours after feeding. The $LT_{50}$ (time to death for 50% of larvae) is 90 hours for larvae fed recombinant virus. At 90 hours, larvae fed wild-type control AcNPV virus are still healthy and feeding normally. This result demonstrates that the recombinant virus is orally active against *Heliothis virescens*.

EXAMPLE 4

Production of AaIT Protein by Expression of the BS-AaIT Gene in *Bombyx mori* Cells in Tissue Culture The recombinant baculovirus carrying the Bs-AaIT gene [described in Example 2] is used to infect *Bombyx mori* cells in culture. AaIT is secreted into the tissue culture medium. The amount of AaIT is measured by isolating the material by HPLC and detecting it with an immunological assay. Medium collected forty-eight hrs post-infection contains about 370 ng AaIT/ml. Injection of this material into *Sarcophaga falculata* larvae demonstrates that this material has neurotoxic activity.

EXAMPLE 5

The recombinant transfer vector pAcUW2 (B).AaIT was constructed in a manner analogous to those already described. Thus, a recombinant, polyhedrin-positive *Autographa californica* NPV was constructed. This is orally infectious and expresses an insect-selective toxin (AaIT), which is isolated from the scorpion *Androctonus australis*, and is under the control of the p10 promoter. This construction was reported by some of us in *Bio/Technology*, 9:848–852 (September 1991). The AaIT toxin gene (sometimes also herein designated "AaHIT") in the transfer vector, pBK283, was digested with SacI and XbaI to excise the complete AaIT gene including a signal sequence of bombyxin required for secretion. The DNA fragment was inserted into the pTZ-18R plasmid between the SacI and XbaI sites (FIG. 16). The plasmid was cleaved with SacI where a synthesized SacI-BamHI-SacI linker (5'-CGGATCCGATCG-3' SEQ. ID NO:42) was inserted. The resulting plasmid contained two BamHI sites; one site near the 5' end of the toxin cDNA and the other site between the stop codon, and XbaI site (FIG. 16) of the original fragment. The insertion of the linker and AaIT gene was confirmed by 1% agarose gel electrophoresis by digestion with BamHI and screening for the resultant 300 base pair fragment. The protocol for GeneClean (BiolO1) was followed in order to isolate the toxin fragment for insertion in the transfer vector with approximately 30% recovery of the DNA fragment.

The excised AaIT gene fragment was ligated into the BgIII cloning site of the digested and dephosphorylated plasmid vector pAcUW2(B), and then transformed in the JM 101 strain of *E. coli*. As a result of the ligation, both the BgIII and BamHI sites were eliminated, and resultant plasmids were screened for a unique SacI site. Three SacI positive clones were identified from sixty colonies using 1% agarose gel electrophoresis. The direction of insertion was confirmed by double digestion with SacI (5' end of the AaIT gene) and BamHI (within the coding sequence of the polyhedrin gene of the transfer vector). Two of three recombinant transfer vectors were carrying the AaIT gene in the correct orientation and had the approximate 1.6 kbp fragment inductive of the correct orientation. The construction resulted in the AaIT cDNA sequence now inserted downstream of a duplicated p10 protein promoter and upstream of the polyhedrin gene 5 producing the recombinant plasmid pAcUW2 (B).AaIT.

Isolation of Recombinant ACNPV.

*Spodoptera frugiperda* cells (Sf-9) were propagated in ExCell 400 media (JF Scientific) supplemented with 2.5% fetal bovine serum. Sf-9 cells were cotransfected by calcium precipitation with the plasmid pAcUW2(B) and polyhedrin negative AcNPV DNA. Polyhedrin-infected cells were identified and collected at 5 days post infection. The recombinant virus was plaque purified by screening for the polyhedrin positive plaques 0.12 Purification of the recombinant virus was expedited by sodium dodecyl sulfate (SDS) treatment (1%) of the cells after each plaque purification in order to eliminate polyhedrin-negative, non-recombinant virus. After purification of the recombinant virus by the initial plaque assay, individual plaques were purified in 3 successive rounds, and the resultant, pure recombinants were propagated and stored at 4° C. and −80° C.

Screening the Recombinant AcUW2(B) AaIT for Biological Activity.

After purification of the recombinant virus by the initial plaque assay, a total of six plaques were isolated and suspended in 500 $\mu$l of ExCell media with 2.5% fetal bovine serum. Sf-9 cells in 35 mm dishes 30 (75% monolayer) were inoculated with 100 $\mu$L (~$10^6$ plaque forming units) of the suspension, and cells were collected 7 days post infection. The individual collections were centrifuged at 1000 g for 5 minutes, and the resulting supernatant was collected and 35 separated from the pelleted cells. The cells were resuspended in double-distilled $H_2O$, treated with 1% SDS, then vortexed for 5 minutes and washed 3 times. Crude estimates of the plaque forming units per ml were determined from the supernatant.

To further demonstrate the insecticidal effects of our new recombinant baculovirus, detailed mortality studies were conducted with 2nd instar *H. virescens* larvae, as described in the Experimental Protocol of the earlier cited paper. Lethal times (LTs) were derived when 2nd instar *H. virescens* larvae were treated with the recombinants AcUW2(B).AaIT, AcUW2(B).JHE and wild-type AcNPV using a common dose of 250 PIBs per plug of diet. The approximate $LT_{50}$ (n=621) of each treatment was 88.0, 143, and 125 hours post infection, respectively. The covariance analysis (C.I.=0.95) shows that there was a significant difference between treatments, and specifically that the recombinant AcUW2(B).AaIT treated larvae had much lower LT values than larvae infected with the other viruses.

Table II shows the dose response and mortality times of second instar *H. virescens* larvae for treatments with AcUW2(B).AaIT and wild-type AcNPV.

TABLE II

| | LD (PIBs) | | | LT (hours) | | |
|---|---|---|---|---|---|---|
| Treatment | 10 | 50 | 90 | 10 | 50 | 90 |
| AcUW2(B) · AaIT | 1.56 | 13.3 | 113 | 59.8[a] | 88.0[a] | 129[a] |
| Wild-Type AcNPV | 2.72 | 21.9 | 175 | 91.4 | 125 | 172 |

[a]Significantly different from other treatments - POLO probit analysis program (C.I. 0.95)
PIBs = polyhedrin inclusion bodies
LT = lethal time; LD = lethal dose These data clearly demonstrate the ability of the AcUW2 (B).AaIT to kill *H. virescens* larvae more quickly than the wild-type ACNPV. The results represent a 30% increase in the speed of kill when compared to wild-type virus.

EXAMPLE 6

In a manner similar to that described in Example 5, we tested the recombinant virus against four different host insects: *Manduca sexta, Trichoplusia ni, Spodoptera exigua*, and *Heliothis virescens*. The recombinant viruses prepared, such as described by the earlier Example 5, significantly increase the speed of killing action.

EXAMPLE 7

Larvae infected with the recombinant AcAaIT typically started showing symptoms of paralysis and stopped feeding 10 to 15 hours prior to death. As a result, these larvae can functionally be considered dead, and treatment with AcAaIT represents an approximately 40% reduction in the time required to kill host larvae when compared to wild-type AcNPV.

We designed experiments to assess the differences in feeding damage that would be incurred by tomato plants infested with larvae of *H. virescens* that had been infected with uninfected controls wild-type AcNPV or AcAaIT. Individual plants were infested with two 4th instar larvae that were uninfected (control, I) or had previously been infected with wild-type AcNPV (II) or /AcAaIT (III) 48 hours earlier. These larvae were allowed to feed continuously on the plants until death.

The AcAaIT treatment resulted in significantly less damaged plants. However, what is not evident is the fact that the larvae infected with AcAaIT were unable to inflict more damage on the tomato plants because they were falling from the plant. In fact, we observed five of eight 4th and 5th instar larvae infected with AcAaIT had fallen from the plant at 120 hours post infection. These individuals were apparently unable to crawl back up the plant due to the onset of paralysis. This is illustrated by FIG. 17. In FIG. 17, panels A illustrate the tomato plants before exposure to any larvae. Panel IA thus shows the control "before" larvae while panel IB shows the control after larvae without any virus had been freely feeding on the plant until the experiment was stopped. As demonstrated by the illustrations (reproduced from photographs), the control tomato plants were badly ravaged by the larvae. Turning to panel IIA, we again see tomato plants before introduction of larvae. In panel IIB larvae infected with wild-type AcNPV have been feeding on the plants for about 190–200 hours at which point the larvae had died and the experiment (for all panels IB, IIB, and IIIB) was stopped. While panel IIB showed considerable improvement over the panel IB control, the plant nevertheless had been subjected to up to about 200 hours of feeding activity before the larvae died. However, turning to panels IIIA (the beginning of the experiment) and IIIB (the end), we see that the panel IIIB plants have considerably more foliage when the experiment was stopped. These plants have more foliage because the inventive baculovirus AcAaIT infected larvae had their behavior disrupted before death so that five of eight larvae fell off the plant after 120 hours of feeding and the remaining three fell shortly thereafter.

Table III confirms that the insects become irritated and were not feeding on the food substrate or were wandering off the substrate a significant amount of time.

TABLE III

Percentage of Time During Course of Infection
Tobacco Budworm Larvae Were Off the Food Substrate

| Food Substrate | AcAaIT | Wild Type Virus |
|---|---|---|
| Cotton | 80.40% | 13.30% |
| Romaine | 64.20% | 15.40% |
| Iceberg | 85.90% | 13.20% |
| Diet | 59.90% | 11.00% |

To obtain the data summarized by Table III, the larvae were droplet fed virus at 2,000 PIBs/$\mu$l as neonates and checked every 6 to 8 hours. Larvae were scored as to whether they were off or on the food substrate as summarized in Table III above. At 64 hours post-infection, over 57% of all tobacco budworm larvae were not on the substrate, versus 32% of wild-type infected insects (which were not yet expressing symptoms). The purpose of this experiment was to confirm that larvae infected with AcAaIT before they die become paralyzed (or have their feeding behavior disrupted), while this does not happen with wild-type infected insects.

It is plausible that low levels of the neurotoxin, AaIT, early in the infection process may irritate the larval host, thus resulting in the "falling" off or eating disruption phenomena. Even though the larva is still potentially capable of feeding and causing damage, it no longer has access to the plant. With the reduced killing time and early immobilization of the host larva by paralysis, AcAaIT appears effectively to curtail food consumption which may translate into reduced feeding damage. As a consequence, use of the recombinant baculovirus can be viewed as providing improved insect control properties, which include enhancing the toxicity of insecticidal microbes (e.g. a faster kill rate) as well as reducing insect pest access to the plant (e.g. early immobilization of the host larvae by paralysis or the "falling" phenomenon).

EXAMPLE 8

As described in the several preceding examples, the recombinant AcNPV, AcAaIT, which we have constructed is orally infective to the most economically important group of lepidopteran pests, the noctuids, which include genera such as Heliothis, Trichoplusia, and Spodoptera. Detailed studies of mortality were conducted using neonate (first instar) larvae of *H. virescens*. Lethal times (LTs) were derived using a common dose of 250 polyhedrin inclusion bodies per plug of diet for the neonates. A dose-response curve (Table IV) of neonate larvae of *H. virescens* illustrates the significant reduction in the time of kill. The $LT_{50}$s for neonate larvae treated with AcAaIT and wild-type AcNPV are 67.3 and 97.9 hpi, respectively. A likelihood ratio test (equal slopes and intercepts, C.I.=0.95) showed a significant difference among treatments. Specifically, the larvae treated with AcAaIT had significantly lower LT values than larvae infected with wild-type AcNPV. These data again represent over a 30% reduction in the rate of kill for AcAaIT when compared with wild-type AcNPV.

TABLE IV

| Treatment[a] | Lethal Times (hours)[b] | | |
|---|---|---|---|
| 1st Instar Larvae | 10 | 50 | 90 |
| AcAaIT | 46.2 | 67.3 | 98.1 |
| | (42.2–49.6) | (54.3–70.4) | (92.2–106) |
| Wild-type AcNPV | 57.1 | 97.9 | 167 |
| | (50.8–62.3) | (91.6–106) | (147–201) |

[a]250 polyhedrin inclusion bodies per plug of diet.
[b]POLO probit analysis program with lower and upper limits (C.I. 0.95).

As a consequence, the preceding examples show that recombinants of the invention work on both neonate and second instar larvae, with the additional "falling off" properties leading to even further improvement in insect control with respect to wild-type baculovirus.

Although the insecticidal properties of recombinant baculoviruses as described have been shown to have improved insecticidal properties, further modifications may be made such as to improve stability of the expressed foreign protein, which could include C-terminal amidation and/or N-terminal pyroglutaminylation. Other modifications, such as the addition of genes from more than one baculovirus or deletion of indigenous genes, can provide tailor-made viruses with increased insecticidal activities. For example, viruses engineered to have quicker replication rates or modified host ranges can be constructed. AcNPV is an excellent candidate for such genetic modifications, since this virus has a comparatively slow replication rate and a broad host range.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

SEQUENCE LISTING

<160> NUMBER OF SEQ ID NOS: 49

<210> SEQ ID NO 1
<211> LENGTH: 64
<212> TYPE: PRT
<213> ORGANISM: Leiurus quinquestriatus hebraeus

<400> SEQUENCE: 1

Val Arg Asp Ala Tyr Ile Ala Lys Asn Tyr Asn Cys Val Tyr Glu Cys
1               5                   10                  15

Phe Arg Asp Ala Tyr Cys Asn Glu Leu Cys Thr Lys Asn Gly Ala Ser
            20                  25                  30

Ser Gly Tyr Cys Gln Trp Ala Gly Lys Tyr Gly Asn Ala Cys Trp Cys
        35                  40                  45

Tyr Ala Leu Pro Asp Asn Val Pro Ile Arg Val Pro Gly Lys Cys Arg
    50                  55                  60

<210> SEQ ID NO 2
<211> LENGTH: 61
<212> TYPE: PRT
<213> ORGANISM: Leiurus quinquestriatus hebraeus

<400> SEQUENCE: 2

Asp Gly Tyr Ile Lys Arg Arg Asp Gly Cys Lys Val Ala Cys Leu Ile
1               5                   10                  15

Gly Asn Glu Gly Cys Asp Lys Glu Cys Lys Ala Tyr Gly Gly Ser Tyr
            20                  25                  30

Gly Tyr Cys Trp Thr Trp Gly Leu Ala Cys Trp Cys Glu Gly Leu Pro
        35                  40                  45

Asp Asp Lys Thr Trp Lys Ser Glu Thr Asn Thr Cys Gly
    50                  55                  60

<210> SEQ ID NO 3
<211> LENGTH: 61
<212> TYPE: PRT
<213> ORGANISM: Leiurus quinquestriatus quinquestriatus

<400> SEQUENCE: 3

```
Asp Gly Tyr Ile Arg Lys Arg Asp Gly Cys Lys Leu Ser Cys Leu Phe
 1               5                  10                  15

Gly Asn Glu Gly Cys Asn Lys Glu Cys Lys Ser Tyr Gly Gly Ser Tyr
                20                  25                  30

Gly Tyr Cys Trp Thr Trp Gly Leu Ala Cys Trp Cys Glu Gly Leu Pro
            35                  40                  45

Asp Glu Lys Thr Trp Lys Ser Glu Thr Asn Thr Cys Gly
        50                  55                  60

<210> SEQ ID NO 4
<211> LENGTH: 61
<212> TYPE: PRT
<213> ORGANISM: Buthotus judaicus

<400> SEQUENCE: 4

Asp Gly Tyr Ile Arg Lys Lys Asp Gly Cys Lys Val Ser Cys Ile Ile
 1               5                  10                  15

Gly Asn Glu Gly Cys Arg Lys Glu Cys Val Ala His Gly Gly Ser Phe
                20                  25                  30

Gly Tyr Cys Trp Thr Trp Gly Leu Ala Cys Trp Cys Glu Asn Leu Pro
            35                  40                  45

Asp Ala Val Thr Trp Lys Ser Ser Thr Asn Thr Cys Gly
        50                  55                  60

<210> SEQ ID NO 5
<211> LENGTH: 64
<212> TYPE: PRT
<213> ORGANISM: Leiurus quinquestriatus hebraeus

<400> SEQUENCE: 5

Val Arg Asp Ala Tyr Ile Ala Lys Asn Tyr Asn Cys Val Tyr Glu Cys
 1               5                  10                  15

Phe Arg Asp Ala Tyr Cys Asn Glu Leu Cys Thr Lys Asn Gly Ala Ser
                20                  25                  30

Ser Gly Tyr Cys Gln Trp Ala Gly Lys Tyr Gly Asn Ala Cys Trp Cys
            35                  40                  45

Tyr Ala Leu Pro Asp Asn Val Pro Ile Arg Val Pro Gly Lys Cys Arg
        50                  55                  60

<210> SEQ ID NO 6
<211> LENGTH: 33
<212> TYPE: PRT
<213> ORGANISM: Scorpio maurus palmatus

<400> SEQUENCE: 6

Ala Leu Pro Leu Ser Gly Glu Tyr Glu Pro Cys Val Arg Pro Arg Lys
 1               5                  10                  15

Cys Lys Pro Gly Leu Val Cys Asn Lys Gln Gln Ile Cys Val Asp Pro
                20                  25                  30

Lys

<210> SEQ ID NO 7
<211> LENGTH: 34
<212> TYPE: PRT
<213> ORGANISM: Scorpio maurus palmatus

<400> SEQUENCE: 7

Val Ser Cys Thr Gly Ser Arg Asp Cys Tyr Ala Pro Cys Lys Arg Gln
 1               5                  10                  15
```

Thr Gly Cys Thr Ser Ala Lys Cys Ile Asn Lys Ser Cys Lys Cys Tyr
            20                  25                  30

Gly Cys

<210> SEQ ID NO 8
<211> LENGTH: 34
<212> TYPE: PRT
<213> ORGANISM: Scorpio maurus palmatus

<400> SEQUENCE: 8

Val Ser Cys Thr Gly Ser Lys Asp Cys Tyr Ala Pro Cys Arg Lys Gln
 1               5                  10                  15

Thr Gly Cys Pro Asn Ala Lys Cys Ile Asn Lys Ser Cys Lys Cys Tyr
            20                  25                  30

Gly Cys

<210> SEQ ID NO 9
<211> LENGTH: 34
<212> TYPE: PRT
<213> ORGANISM: Scorpio maurus palmatus

<400> SEQUENCE: 9

Val Ser Cys Thr Gly Ser Lys Glu Cys Tyr Ala Pro Cys Lys Lys Gln
 1               5                  10                  15

Thr Gly Cys Pro Asn Ala Lys Cys Met Asn Arg Lys Cys Lys Cys Tyr
            20                  25                  30

Gly Cys

<210> SEQ ID NO 10
<211> LENGTH: 226
<212> TYPE: DNA
<213> ORGANISM: African scorpion Androctonus australis

<400> SEQUENCE: 10
gatccaaata atgaaaaaaa acggctacgc tgttgactct tctggcaaag ctccggaatg     60
cctgctgtct aactactgca caaccagtg cactaaagtt cattacgctg acaaaggcta    120
ctgctgcctg ctgtcttgct actgcttcgg cctgaacgac gacaaaaaag ttctggaaat    180
ctctgacact cgtaaatctt actgcgacac tactatcaac taatag                   226

<210> SEQ ID NO 11
<211> LENGTH: 225
<212> TYPE: DNA
<213> ORGANISM: African scorpion Androctonus australis

<400> SEQUENCE: 11
gatcctatta gttgatagta gtgtcgcagt aagatttacg agtgtcagag attccagaac     60 tttttttgtcg tcgttcaggc cgaagcagta gcaagacagc aggcagcagt agcctttgtc   120
agcgtaatga actttagtgc actggttgtt gcagtagtta gacagcaggc attccggagc    180
tttgccagaa gagtcaacag cgtagccgtt tttttttcatt atttg                   225

<210> SEQ ID NO 12
<211> LENGTH: 24
<212> TYPE: DNA
<213> ORGANISM: African scorpion Androctonus australis

<400> SEQUENCE: 12
gatccaaata atgaaaaaaa acgg                                            24

<210> SEQ ID NO 13
<211> LENGTH: 20
<212> TYPE: DNA
<213> ORGANISM: African scorpion Androctonus australis

<400> SEQUENCE: 13
ctacgctgtt gactcttctg                                               20

<210> SEQ ID NO 14
<211> LENGTH: 20
<212> TYPE: DNA
<213> ORGANISM: African scorpion Androctonus australis

<400> SEQUENCE: 14
gcaaagctcc ggaatgcctg                                               20

<210> SEQ ID NO 15
<211> LENGTH: 20
<212> TYPE: DNA
<213> ORGANISM: African scorpion Androctonus australis

<400> SEQUENCE: 15
ctgtctaact actgcaacaa                                               20

<210> SEQ ID NO 16
<211> LENGTH: 20
<212> TYPE: DNA
<213> ORGANISM: African scorpion Androctonus australis

<400> SEQUENCE: 16
ccagtgcact aaagttcatt                                               20

<210> SEQ ID NO 17
<211> LENGTH: 20
<212> TYPE: DNA
<213> ORGANISM: African scorpion Androctonus australis

<400> SEQUENCE: 17
acgctgacaa aggctactgc                                               20

<210> SEQ ID NO 18
<211> LENGTH: 20
<212> TYPE: DNA
<213> ORGANISM: African scorpion Androctonus australis

<400> SEQUENCE: 18
tgcctgctgt cttgctactg                                               20

<210> SEQ ID NO 19
<211> LENGTH: 20
<212> TYPE: DNA
<213> ORGANISM: African scorpion Androctonus australis

<400> SEQUENCE: 19
cttcggcctg aacgacgaca                                               20

<210> SEQ ID NO 20
<211> LENGTH: 20
<212> TYPE: DNA
<213> ORGANISM: African scorpion Androctonus australis

<400> SEQUENCE: 20
aaaaagttct ggaaatctct                                               20

<210> SEQ ID NO 21
<211> LENGTH: 20
<212> TYPE: DNA
<213> ORGANISM: African scorpion Androctonus australis

<400> SEQUENCE: 21
gacactcgta aatcttactg                                               20

<210> SEQ ID NO 22
<211> LENGTH: 22
<212> TYPE: DNA
<213> ORGANISM: African scorpion Androctonus australis

<400> SEQUENCE: 22
cgacactact atcaactaat ag                                            22

<210> SEQ ID NO 23
<211> LENGTH: 25
<212> TYPE: DNA
<213> ORGANISM: African scorpion Androctonus australis

<400> SEQUENCE: 23
cgtagccgtt tttttcatt atttg                                          25

<210> SEQ ID NO 24
<211> LENGTH: 20
<212> TYPE: DNA
<213> ORGANISM: African scorpion Androctonus australis

<400> SEQUENCE: 24
tttgccagaa gagtcaacag                                               20

<210> SEQ ID NO 25
<211> LENGTH: 20
<212> TYPE: DNA
<213> ORGANISM: African scorpion Androctonus australis

<400> SEQUENCE: 25
gacagcaggc attccggagc                                               20

<210> SEQ ID NO 26
<211> LENGTH: 20
<212> TYPE: DNA
<213> ORGANISM: African scorpion Androctonus australis

<400> SEQUENCE: 26
actggttgtt gcagtagtta                                               20

<210> SEQ ID NO 27
<211> LENGTH: 20
<212> TYPE: DNA
<213> ORGANISM: African scorpion Androctonus australis

<400> SEQUENCE: 27
agcgtaatga actttagtgc                                               20

<210> SEQ ID NO 28
<211> LENGTH: 20
<212> TYPE: DNA
<213> ORGANISM: African scorpion Androctonus australis

<400> SEQUENCE: 28

-continued aggcagcagt agcctttgtc                                              20

<210> SEQ ID NO 29
<211> LENGTH: 20
<212> TYPE: DNA
<213> ORGANISM: African scorpion Androctonus australis

<400> SEQUENCE: 29
cgaagcagta gcaagacagc                                              20

<210> SEQ ID NO 30
<211> LENGTH: 20
<212> TYPE: DNA
<213> ORGANISM: African scorpion Androctonus australis

<400> SEQUENCE: 30 tttttttgtcg tcgttcaggc                                             20

<210> SEQ ID NO 31
<211> LENGTH: 20
<212> TYPE: DNA
<213> ORGANISM: African scorpion Androctonus australis

<400> SEQUENCE: 31
gtgtcagaga tttccagaac                                              20

<210> SEQ ID NO 32
<211> LENGTH: 20
<212> TYPE: DNA
<213> ORGANISM: African scorpion Androctonus australis

<400> SEQUENCE: 32
tgtcgcagta agatttacga                                              20

<210> SEQ ID NO 33
<211> LENGTH: 21
<212> TYPE: DNA
<213> ORGANISM: African scorpion Androctonus australis

<400> SEQUENCE: 33
gatcctatta gttgatagta g                                            21

<210> SEQ ID NO 34
<211> LENGTH: 226
<212> TYPE: DNA
<213> ORGANISM: African scorpion Androctonus australis

<400> SEQUENCE: 34
gatccaaata atgaaaaaaa acggctacgc tgttgactct tctggcaaag ctccggaatg     60
cctgctgtct aactactgca caaccagtg cactaaagtt cattacgctg acaaggcta    120 ctgctgcctg ctgtcttgct actgcttcgg cctgaacgac gacaaaaaag ttctggaaat   180
ctctgacact cgtaaatctt actgcgacac tactatcaac taatag                 226

<210> SEQ ID NO 35
<211> LENGTH: 36
<212> TYPE: DNA
<213> ORGANISM: Bombyx mori

<400> SEQUENCE: 35
tgttgacacc cacattactg ttgacaacat taatgc                             36

```
<210> SEQ ID NO 36
<211> LENGTH: 36
<212> TYPE: DNA
<213> ORGANISM: Bombxy mori

<400> SEQUENCE: 36
tagagctcat gaagatactc cttgctattg cattaa                              36

<210> SEQ ID NO 37
<211> LENGTH: 36
<212> TYPE: DNA
<213> ORGANISM: African scorpion Androctonus australis

<400> SEQUENCE: 37
aatctagagg atcctagttg atgatagtag tgtcgc                              36

<210> SEQ ID NO 38
<211> LENGTH: 36
<212> TYPE: DNA
<213> ORGANISM: African scorpion Androctonus australis

<400> SEQUENCE: 38
gtaatgtggg tgtcaacaaa aaaaaacggc tacgct                              36

<210> SEQ ID NO 39
<211> LENGTH: 287
<212> TYPE: DNA
<213> ORGANISM: Artificial Sequence
<220> FEATURE:
<223> OTHER INFORMATION: This encodes for a chimeric protein comprising
      a Bombyx mori signal sequence and an Androctonus australis
      peptide.

<400> SEQUENCE: 39
gagctcatga agatactcct tgctattgca ttaatgttgt caacagtaat gtgggtgtca    60
acaaaaaaaa acggctacgc tgttgactct tctggcaaag ctccggaatg cctgctgtct   120
aactactgca caaccagtg cactaaagtt cattacgctg acaaaggcta ctgctgcctg   180
ctgtcttgct actgcttcgg cctgaacgac gacaaaaaag ttctggaaat ctctgacact   240
cgtaaatctt actgcgacac tactatcatc aactaggatc ctctaga              287

<210> SEQ ID NO 40
<211> LENGTH: 15
<212> TYPE: DNA
<213> ORGANISM: Artificial Sequence
<220> FEATURE:
<223> OTHER INFORMATION: Synthesized oligonucleotide comprising a SacI
      site and a transcriptional start signal.

<400> SEQUENCE: 40
gagctcgaat tcatg                                                    15

<210> SEQ ID NO 41
<211> LENGTH: 12
<212> TYPE: DNA
<213> ORGANISM: Artificial Sequence
<220> FEATURE:
<223> OTHER INFORMATION: This represents a synthetic oligonucleotide
      that introduces a BamHI site when inserted into a vector.

<400> SEQUENCE: 41
cggatccgat cg                                                       12

<210> SEQ ID NO 42
```

```
<211> LENGTH: 12
<212> TYPE: DNA
<213> ORGANISM: Artificial Sequence
<220> FEATURE:
<223> OTHER INFORMATION: This represents a synthetic oligonucleotide
      which comprises a SacI-BamHI-SacI linker.

<400> SEQUENCE: 42
cggatccgat cg                                                          12

<210> SEQ ID NO 43
<211> LENGTH: 197
<212> TYPE: DNA
<213> ORGANISM: Leuirus quinquestriatus hebraeus

<400> SEQUENCE: 43
gatccatgga cggctacatc aagcgccgcg acggctgcaa ggtggcttgc ctgatcggca       60
acgagggctg cgacaaggag tgcaaggctt acggcggcag ctacggctac tgctggacct     120
ggggcctggc ttgctggtgc gagggcctgc cggacgacaa gacctggaag agcgagacca     180
acacctgcgg ctaatag                                                    197

<210> SEQ ID NO 44
<211> LENGTH: 264
<212> TYPE: DNA
<213> ORGANISM: African scorpion Androctonus australis

<400> SEQUENCE: 44
gaattcattc aagatacaac atttctccta tagtcatgaa aaaaacggc tacgctgttg        60 actcttctgg caaagctccg gaatgcctgc tgtctaacta ctgcaacaac cagtgcacta     120
aagttcatta cgctgacaaa ggctactgct gcctgctgtc ttgctactgc ttcggcctga     180
acgacgacaa aaaagttctg gaaatctctg acactcgtaa atcttactgc gacactacta     240
tcatcaacta gtaatctaga attc                                            264

<210> SEQ ID NO 45
<211> LENGTH: 70
<212> TYPE: PRT
<213> ORGANISM: African scorpion Androctonus australis

<400> SEQUENCE: 45

Met Lys Lys Asn Gly Tyr Ala Val Asp Ser Ser Gly Lys Ala Pro Glu
1               5                   10                  15

Cys Leu Leu Ser Asn Tyr Cys Asn Asn Gln Cys Thr Lys Val His Tyr
                20                  25                  30

Ala Asp Lys Gly Tyr Cys Cys Leu Leu Ser Cys Tyr Cys Phe Gly Leu
            35                  40                  45

Asn Asp Asp Lys Lys Val Leu Glu Ile Ser Asp Thr Arg Lys Ser Tyr
        50                  55                  60

Cys Asp Thr Thr Ile Asn
65                  70

<210> SEQ ID NO 46
<211> LENGTH: 62
<212> TYPE: PRT
<213> ORGANISM: Leuirus quinquestriatus hebraeus

<400> SEQUENCE: 46

Met Asp Gly Tyr Ile Lys Arg Arg Asp Gly Cys Lys Val Ala Cys Leu
1               5                   10                  15
```

-continued

```
Ile Gly Asn Glu Gly Cys Asp Lys Glu Cys Lys Ala Tyr Gly Gly Ser
            20                  25                  30

Tyr Gly Tyr Cys Trp Thr Trp Gly Leu Ala Cys Trp Cys Glu Gly Leu
        35                  40                  45

Pro Asp Asp Lys Thr Trp Lys Ser Glu Thr Asn Thr Cys Gly
    50                  55                  60

<210> SEQ ID NO 47
<211> LENGTH: 89
<212> TYPE: PRT
<213> ORGANISM: Artificial Sequence
<220> FEATURE:
<223> OTHER INFORMATION: This represents a chimeric protein comprising a
      Bombyx mori signal sequence and an Androctonus
      australis peptide.

<400> SEQUENCE: 47

Met Lys Ile Leu Leu Ala Ile Ala Leu Met Leu Ser Thr Val Met Trp
 1               5                  10                  15

Val Ser Thr Lys Lys Asn Gly Tyr Ala Val Asp Ser Ser Gly Lys Ala
            20                  25                  30

Pro Glu Cys Leu Leu Ser Asn Tyr Cys Asn Asn Gln Cys Thr Lys Val
        35                  40                  45

His Tyr Ala Asp Lys Gly Tyr Cys Cys Leu Leu Ser Cys Tyr Cys Phe
    50                  55                  60

Gly Leu Asn Asp Asp Lys Lys Val Leu Glu Ile Ser Asp Thr Arg Lys
65                  70                  75                  80

Ser Tyr Cys Asp Thr Thr Ile Ile Asn
                85

<210> SEQ ID NO 48
<211> LENGTH: 71
<212> TYPE: PRT
<213> ORGANISM: African scorpion Androctonus australis

<400> SEQUENCE: 48

Met Lys Lys Asn Gly Tyr Ala Val Asp Ser Ser Gly Lys Ala Pro Glu
 1               5                  10                  15

Cys Leu Leu Ser Asn Tyr Cys Asn Asn Gln Cys Thr Lys Val His Tyr
            20                  25                  30

Ala Asp Lys Gly Tyr Cys Cys Leu Leu Ser Cys Tyr Cys Phe Gly Leu
        35                  40                  45

Asn Asp Asp Lys Lys Val Leu Glu Ile Ser Asp Thr Arg Lys Ser Tyr
    50                  55                  60

Cys Asp Thr Thr Ile Ile Asn
65                  70

<210> SEQ ID NO 49
<211> LENGTH: 49
<212> TYPE: DNA
<213> ORGANISM: Artificial Sequence
<220> FEATURE:
<223> OTHER INFORMATION: This represents a synthetic oligonucleotide
      comprising restriction sites for insertion into a
      vector.

<400> SEQUENCE: 49
aaaacctata agggtaccga gctcgaattc tagataggcc ttaaaacac                49
```

It is claimed:

1. A recombinant nuclear polyhedrosis virus which, in insect cells infected therewith, expresses a foreign protein, the foreign protein being an insecticidal toxin, or a functional derivative thereof, the nuclear polyhedrosis virus genome having an intact polyhedrin gene and provided with a secretion signal sequence for secreting the foreign protein.

2. The recombinant nuclear polyhedrosis virus as in claim 1 wherein the toxin is a scorpion toxin.

3. The recombinant nuclear polyhedrosis virus as in claim 1 wherein the toxin is AaIT, a chactoid scorpion toxin or a Buthoid scorpion toxin.

4. The recombinant nuclear polyhedrosis virus as in claim 1 wherein the foreign protein is an arthropod derived venom.

5. The recombinant nuclear polyhedrosis virus as in claim 1 wherein the foreign protein enhances the insecticidal activity of the recombinant with respect to wild type when the foreign protein is expressed in insect cells infected therewith.

6. The nuclear polyhedrosis virus as in claim 2 wherein the nuclear polyhedrosis virus is *Autographa californica* nuclear polyhedrosis virus.

7. A recombinant baculovirus wherein the virus is *Autographa californica* nuclear polyhedrosis virus, which in insect cells infected therewith, expresses an AaIT toxin, or a functional derivative thereof, by secretion.

8. A method of preparing nuclear polyhedrosis viruses with an intact polyhedrin gene and an improved insect control property, comprising:

cloning a chimeric gene encoding an insecticidal toxin, the toxin being a foreign protein to an insect host, the chimeric gene comprising a genetic sequence coding for the toxin, or a functional derivative thereof, and a signal peptide, into a baculovirus transfer vector at a restriction site down stream of a promotor; and introducing the chimeric gene into the genome of a nuclear polyhedrosis virus without disrupting the polyhedrin gene, wherein the chimeric gene when expressed in the insect host provides improved toxicity with respect to the wild type nuclear polyhedrosis virus.

9. The method as in claim 8 wherein the toxin is AaIT.

10. The method as in claim 8 or 9 wherein the baculovirus is *Autographa californica* nuclear polyhedrosis virus.

11. The method as in claim 10 wherein the improved insect control property is an increased kill rate with respect to wild type baculovirus.

12. The method as in claim 10 wherein the improved insect control property is more rapid onset of feeding cessation.

13. A method for enhancing the toxicity of a nuclear polyhedrosis virus, comprising:

isolating a recombinant DNA molecule having a genetic sequence coding for an insect-selective protein neurotoxin; and introducing the recombinant DNA molecule into the genome of the nuclear polyhedrosis virus without disrupting the polyhedrin gene, wherein the insect-selective protein neurotoxin provides enhanced toxicity when expressed in insect cells infected therewith with respect to wild-type.

14. The method as in claim 13 wherein the genetic sequence coding for an insect-selective protein neurotoxin is derived from venom.

15. The method as in claim 14 wherein the venom is derived from scorpions, wasps, snails, or spiders.

16. The recombinant nuclear polyhedrosis virus as in claim 1 or 4 wherein the recombinant is a hybrid having a host range expanded with respect to wild type virus.

17. The recombinant nuclear polyhedrosis virus as in claim 5 wherein the infection is via oral ingestion of the recombinant by insects.

* * * * *

UNITED STATES PATENT AND TRADEMARK OFFICE
CERTIFICATE OF CORRECTION

PATENT NO. : 6,689,356 B1
DATED : February 10, 2004
INVENTOR(S) : Zlotkin et al.

It is certified that error appears in the above-identified patent and that said Letters Patent is hereby corrected as shown below:

<u>Title page,</u>
Item [*] Notice, delete "Subject to any disclaimer, the term of this patent is extended or adjusted under 35 U.S. 154(b) by 102 days."

Signed and Sealed this

Eighteenth Day of May, 2004

JON W. DUDAS
*Acting Director of the United States Patent and Trademark Office*